US00PP32459P3

(12) United States Plant Patent
Mehlenbacher et al.

(10) Patent No.: US PP32,459 P3
(45) Date of Patent: Nov. 17, 2020

(54) ***CORYLUS* PLANT NAMED 'POLLYO'**

(50) Latin Name: ***Corylus avellana* cultivar**
Varietal Denomination: PollyO

(71) Applicant: Oregon State University, Corvallis, OR (US)

(72) Inventors: Shawn A. Mehlenbacher, Corvallis, OR (US); David C. Smith, Corvallis, OR (US); Rebecca L. McCluskey, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 120 days.

(21) Appl. No.: 15/998,094

(22) Filed: Jun. 29, 2018

(65) Prior Publication Data

US 2020/0008334 P1 Jan. 2, 2020

(51) Int. Cl.
*A01H 5/08* (2018.01)
*A01H 6/00* (2018.01)

(52) U.S. Cl.
USPC ..... Plt./152
CPC ..... *A01H 6/00* (2018.05); *A01H 5/08* (2013.01)

(58) Field of Classification Search
USPC ..... Plt./152
CPC ..... A01H 5/00; A01H 5/08; A01H 5/0825
See application file for complete search history.

(56) References Cited

PUBLICATIONS https://www.capitalpress.com/state/oregon/new-hazelnut-variety-nanned-for-industry-official/article_076b181c-449a-56cb-b0f8-60645024787f.html; Jan. 22, 2018; 3 pages.*

* cited by examiner

*Primary Examiner* — Kent L Bell
(74) *Attorney, Agent, or Firm* — Klarquist Sparkman, LLP

(57) ABSTRACT

A new and distinct *Corylus* plant named 'PollyO' is characterized by high nut yield, early nut maturity, small round nuts and kernels, high kernel percentage, good kernel blanching and excellent flavor. The tree is vigorous and has a desirable growth habit. 'PollyO' is resistant to bud mite (primarily *Phytoptus avellanae* Nal.). DNA markers and field exposure indicate that it is highly resistant to eastern filbert blight (EFB) caused by *Anisogramma anomala* (Peck) E. Müller.

12 Drawing Sheets

Specification includes a Sequence Listing.

ACKNOWLEDGMENT OF GOVERNMENT SUPPORT

This invention was made with government support under USDA/ARS 58-5358-4-025, USDA-NIFA-SCRI 2009-51181-06028, USDA-NIFA-AFRI 2014-67013-22421, and USDA-NIFA-SCRI 2016-04991 awarded by the United States Department of Agriculture. The government has certain rights in the invention.

INCORPORATION OF ELECTRONIC SEQUENCE LISTING

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file, created on Aug. 6, 2018, 8 KB, which is incorporated by reference herein.

BACKGROUND

The present Invention relates to a new and distinct cultivar of *Corylus* plant, botanically known as *Corylus avellana*, and hereinafter referred to by the name 'PollyO'.

The new *Corylus* resulted from a controlled cross of OSU 684.104×OSU 669.104 made in 2001 (FIG. 1); the progeny was designated 01021. OSU 684.104 is from a cross of 'Birk 5-39' (unpatented) and 'Mortarella' (unpatented). 'Birk 5-39', an OSU selection growing in a small plot near Canby, Oreg., is from a cross of OSU 14.084 ('Barcelona'×'Daviana', both unpatented) and 'Negret' (unpatented). OSU 669.104 is a full sib of the pollinizer 'Zeta' (unpatented). OSU 669.104 carries a dominant allele for a very high level of resistance to eastern filbert blight (EFB) from the grower selection 'Zimmerman' (unpatented). Microsatellite marker analysis indicates that 'Zimmerman' is from a cross of 'Barcelona' and the EFB-resistant pollinizer 'Gasaway' (Gökirmak et al., Characterization of European hazelnut (*Corylus avellana*) cultivars using SSR markers. Genetic Resources and Crop Evolution 56:147-172, 2009) (unpatented). The pedigree of 'PollyO' includes germplasm from Spain ('Barcelona', 'Casina', and 'Negret', all unpatented), Italy ('Mortarella' and 'Montebello', both unpatented) and England ('Daviana').

Hybrid seeds from the controlled cross were harvested in August 2001, stratified, and the resulting seedlings grown in a glasshouse during the summer of 2002. 99 seedlings from this cross were planted in the field in Corvallis, Oreg. in October 2002. The designation OSU 1108.001 indicates the row and tree location of the original seedling. Nuts were first observed on the original seedling in September 2006. The nuts were harvested from the original seedling tree and evaluated over four years (2006-2009).

'PollyO' was propagated by tie-off layerage of the suckers in the summer beginning in 2008. The rooted layers from the first propagation (2008) were lined out in a nursery row the year after layerage (2009), and used to plant a replicated yield trial the following spring (2010). The first trial included four trees of each variety. EFB-susceptible selections and check cultivars 'Barcelona', 'Clark' and 'Sacajawea' (unpatented) (Mehlenbacher et al., 2008. 'Sacajawea' hazelnut. *HortScience* 43:255-257) were planted on the same date in a trial adjacent to the first trial. Fungicides were applied to the trial of susceptible genotypes to reduce the incidence of EFB. The rooted layers from the second propagation (2009) were lined out in a nursery row in 2010 and used to plant a second trial in 2011. The second trial had seven blocks. Both trials were planted as randomized complete block designs with a single tree of each genotype in each block. EFB-resistant cultivars 'Jefferson' (unpatented) (Mehlenbacher et al., 2011. 'Jefferson' hazelnut. *HortScience* 46:662-664), 'Yamhill' (unpatented) (Mehlenbacher et al., 2009. 'Yamhill' hazelnut. *HortScience* 44:845-847) and 'Gamma' (unpatented) (Mehlenbacher and Smith. 2004. Hazelnut pollenizers 'Gamma', 'Delta', 'Epsilon' and 'Zeta'. HortScience 39:1498-1499) served as checks in the first trial, while 'Jefferson' and 'Yamhill' were the checks in the second trial. Both trials included additional EFB-resistant selections.

The new cultivar was asexually reproduced by tie-off layerage of the suckers in the summer of 2008 and 2009 in Corvallis, Oreg. It was moved with a tree spade to the layer beds in spring, 2010. Of the 12 layers harvested in 2008, three were well-rooted, seven had a modest number of roots, and two had no roots. The size (caliper) was rated as medium. Layers harvested in 2009 showed improved rooting. Further propagation by layerage of about 28 suckers per year was performed in 2011-14, of which 39% were rated as well-rooted, 26% with fair rooting, 26% with poor rooting and 9% with no roots. In general, the layers rooted sufficiently well and size (caliper) was medium to small. The unique features of this new *Corylus* are stable and reproduced true-to-type in successive generations of asexual reproduction.

SUMMARY

The following traits have been observed and are determined to be the unique characteristics of 'PollyO'. 'PollyO' is well-suited to the blanched kernel market for use in chocolate products and baked goods. 'PollyO' combines high nut yield, early nut maturity, small round nuts and kernels, high kernel percentage, good kernel blanching and excellent flavor. The tree is vigorous and has a desirable growth habit. 'PollyO' is resistant to bud mite (primarily *Phytoptus avellanae* Nal.). DNA markers and field exposure indicate that it is highly resistant to eastern filbert blight (EFB) caused by *Anisogramma anomala* (Peck) E. Müller. The resistance is conferred by a dominant allele from 'Zimmerman', which microsatellite markers indicate is from a cross of 'Barcelona'×'Gasaway' (Gökirmak et al., Characterization of European hazelnut (*Corylus avellana*) cultivars using SSR markers. Genetic Resources and Crop Evolution 56:147-172, 2009). EFB is now present throughout the Willamette Valley where 99% of the U.S. hazelnut crop is grown. Pruning to remove cankers and fungicide applications are currently used to manage the disease in orchards of 'Barcelona' and other susceptible cultivars. 'PollyO' is suitable for planting in areas with high disease pressure, as are previous releases 'Yamhill' (2008, unpatented), 'Jefferson' (2009, unpatented), 'Dorris' (2012, US Plant Patent No. PP25,022) (Mehlenbacher et al., 2013. 'Dorris' hazelnut. *HortScience* 48:796-799), 'Wepster' (2013, US Plant Patent No. PP27,141) (Mehlenbacher et al., 2014. 'Wepster' hazelnut. *HortScience* 49:346-349) and 'McDonald' (2014, US Plant Patent No. PP28,200) (Mehlenbacher et al., 2016. 'McDonald' hazelnut. HortScience 51:757-760).

'PollyO' has incompatibility alleles $S_2$ and $S_{10}$. Both alleles are expressed in the stigmas, but only $S_{10}$ is expressed in the pollen because of dominance. Female receptivity is early, with 'Wepster' and 'McDonald', while pollen is shed by 'PollyO' about ten days later than the other two. Pollen germination is high and similar to 'Wepster' and 'McDonald'. Recommended pollinizers include 'Wepster' ($S_1$ $S_2$), 'McDonald' ($S_2$ $S_{15}$) and 'York' ($S_2$ $S_{21}$) (US Plant Patent No. PP24,972).

'PollyO' can serve as a companion for 'Wepster' and 'McDonald', and an alternative to 'Yamhill'. Many growers find 'Yamhill' trees difficult to manage because of low vigor, and the kernels do not blanch well. 'Wepster' and 'McDonald' are cross-compatible with 'PollyO' in all directions, giving growers additional options in orchard design. All three cultivars ('Wepster', 'McDonald' and 'PollyO') could be planted together with each serving as a pollinizer for the others.

Comparisons in two replicated trials conducted in Corvallis, Oreg., plants of 'PollyO' differed from plants of other cultivars and selections of *Corylus avellana* known to the Inventors primarily in nut yield, time of nut maturity, nut size, and kernel percentage (ratio of kernel weight to nut weight). For example:

- Nut yield (kg per tree): First trial: 'PollyO' (29.39), 'Jefferson' (24.26), and 'Yamhill' (26.47); second trial 'PollyO' (23.46), 'Jefferson' (16.91), and 'Yamhill' (21.69);
- Nut maturity: 'PollyO' nuts mature 10-14 days earlier than 'Barcelona', a few days earlier than 'Yamhill';
- Nut size (L×W×D): 'PollyO' (19.5 mm×19.8 mm×17.2 mm), 'McDonald' (18.4 mm×18.9 mm×17.9 mm), 'Wepster' (18.3 mm×19 mm×16.6 mm) (see also FIG. 14); and
- Kernel Percentage: 'PollyO' (47.9%), 'McDonald' (51.5%), 'Wepster' (43.9%), 'Felix' (50.1%), 'Dorris' (43.0%), and 'Barcelona' (43.0%).

BRIEF DESCRIPTION OF THE DRAWINGS

The accompanying colored photographs illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

FIG. 10 shows the time of female receptivity (bottom, red) and pollen shed (top, green) of 'PollyO' (OSU 1108.001) and other hazelnut cultivars in a trial planted in 2011 (December 2014-March 2015).

FIG. 12 shows the time of female receptivity (bottom, red) and pollen shed (top, green) of 'PollyO' (OSU 1108.001) and other hazelnut cultivars in a trial planted in 2011 (December 2016-March 2017).

SEQUENCE LISTING

Figure 1:
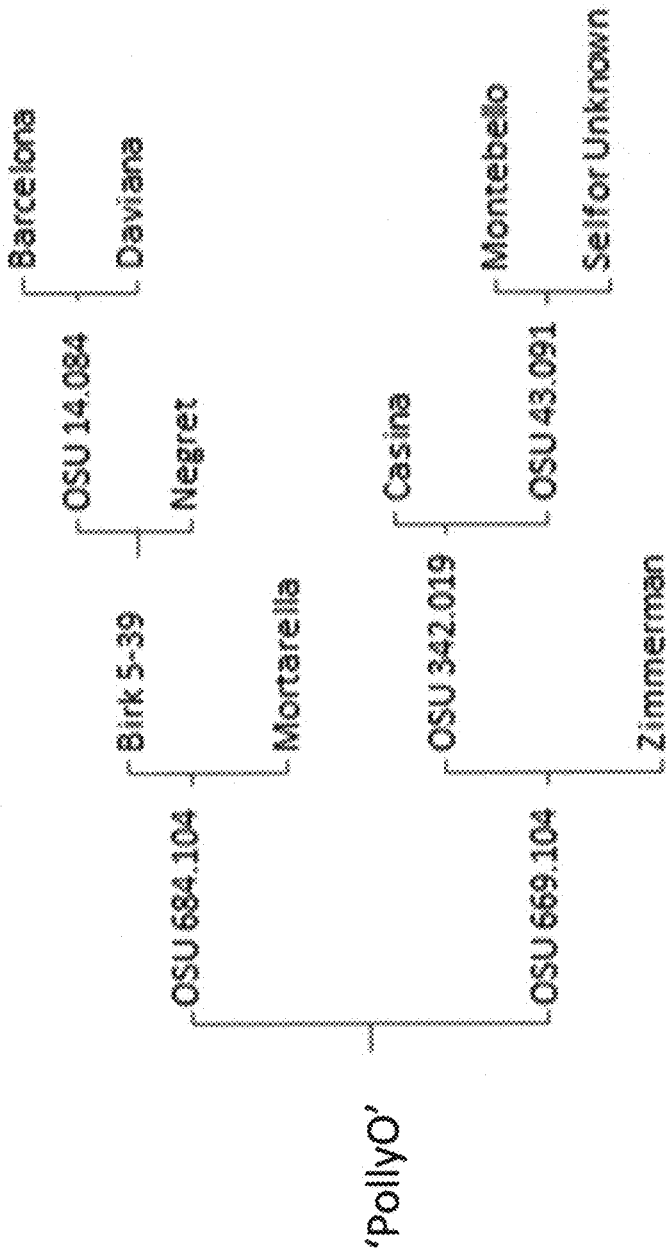
FIG. 1 provides the pedigree of the 'PollyO' (OSU 1108.001) hazelnut tree. The pedigree of the female parent OSU 684.104 and the male parent OSU 669.104 are shown.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NOS: 1-40 are primer sequences that can be used for genetic fingerprinting.

DETAILED DESCRIPTION

The cultivar 'PollyO' has not been observed under all possible environmental conditions. The phenotype may vary somewhat with variations in environment such as temperature and light intensity, without, however, any variance in genotype. The aforementioned photographs and following observations and measurements describe trees grown in Corvallis, Oreg. under commercial practice outdoors in the field during the fall, winter and spring. Plants used for the photographs and description were propagated by tie-off layerage and growing on their own roots, and seven or eight years old. In the following description, color references are made to The Royal Horticultural Society Colour Chart, 1966 Edition, except where general terms of ordinary dictionary significance are used. The list of UPOV descriptors are from the Mar. 28, 1979 Hazelnut guidelines from UPOV, unless otherwise noted.

Botanical Classification:

*Corylus avellana* cultivar 'PollyO'.

Parentage:

Female, or seed, parent: *Corylus avellana* cultivar OSU 684.104

Male, or pollen, parent: *Corylus avellana* cultivar OSU 669.104

Comparison to Parents:

'PollyO' differs from both parents for alleles at the incompatibility alleles. 'PollyO' differs from its female parent OSU 684.104 in that it is resistant to eastern filbert blight. 'PollyO' nuts mature 17 days before those of its male parent OSU 669.104.

Propagation (Type Rooted Suckers):

Time to initiate roots: About 30 days at 20° C.

Time to produce a rooted young plant: About six months at 22° C.

Root description. Fine to thick; freely branching; creamy white in color.

Propagation (Type Whip Grafting):

Time to budbreak on the scions: About 14 days at 25° C.

Time to produce a grafted plant: About six months at 25° C.

Plant Description:

General appearance: natural habit is a perennial shrub, but in commercial orchards, is a single trunk tree. Upright-spreading plant habit.

Growth and branching habit: Freely branching; about 15 lateral branches develop per plant. Pinching, that is, removal of the terminal apices, enhances branching with lateral branches potentially forming at every node.

Vigor: Strong vigor

Growth habit. semi-erect

Size: Plant height is about 5 meters; plant diameter or spread is about 5 meters.

Trunk diameter at the end of the seventh leaf, averaged over two trials=12.14 cm.

Trunk color: 177D.

Trunk texture: smooth.

Lateral Branch Description:

Length: About 45.6 cm.

Diameter: About 4.4 mm.

Internode length: About 3.4 mm.

Texture: Smooth, glabrous.

Strength: Strong.

Color, immature: 139D.

Color, mature: 177D.

Foliage Description:

Arrangement: Alternate, simple.

Length: About 13.3 cm.

Width: About 11.8 cm.

Shape: Oblong to ovate.

Apex: Obtuse to acute.

Base: Cordate.

Margin: Serrate.

Texture, upper and lower surfaces: Slightly pubescent.

Venation pattern: Pinnate.

Color: Developing foliage, upper surface 141C, lower surfaces: 139C. Fully expanded foliage, upper surface: Spring, summer, and fall 146A; Fully expanded foliage, lower surface: Spring, summer, and fall, 146B. Venation, upper surface: Spring, summer, and fall, 146A. Venation, lower surface: Spring, summer, and fall, 146D.

Leaf Bud Description:

Shape: ovoid

Time of leaf budbreak: descriptor=6 (medium to late).

Color: 143C

Length is 6.4 mm, and width is 4.0 mm.

Petiole Description:

Length: About 16.3 mm.

Diameter: About 1.6 mm.

Texture, upper and lower surfaces: Pubescent.

Color, upper surface: Spring, summer, and fall, 146C.

Color, lower surface: Spring, summer, and fall, 146D.

Flower Description:

Male inflorescences are catkins, color prior to elongation 138B.

Catkin length: 20.1 mm

Catkin width (diameter): 5.4 mm

Female inflorescence style color 047B (with reference to the Voss and Hale, HortScience 33:13-17, 1998).

Time of female flowering: descriptor=6 (medium to late)

Time of female flowering compared to male flowering: protogyny (descriptor=2, same time).

Involucre constriction: absent

Involucre length: 1.25 times length of nut.

Size of indentation: descriptor=5 (medium)

Strength of serration of indentation: descriptor=5 (medium)

Pubescence on husk: descriptor=9 (present)

Thickness of callus at base: descriptor=7 (thick)

Jointing of bracts: descriptor=1 (absent)

Female inflorescences are modified leaf buds, with a color of 143C.

Nut Description:

Length: About 19.5 mm.

Width: About 19.8 mm.

Depth: About 17.2 mm.

Nut shape: Round. Nut shape index [(Width+Depth)/2*Length]=0.950. Nut compression index (Width/Depth)=1.15.

Nut shell color: 164A.

Nut shell texture: smooth.

Nut weight: About 2.88 grams.

Kernel weight: About 1.38 grams.

Kernel percentage (kernel weight/nut weight): About 47.9%.

Kernel length: from base to apex 19.2 mm.

Kernel width: at widest point 19.3 mm.

Kernel depth: perpendicular to width 17.4 mm.

Kernel texture: smooth.

Kernel pellicle color: brown 165C.

Number of fruits per cluster: 4.

Number of stripes on shell: descriptor=3 (few).

Prominence of fruit apex: slightly prominent, descriptor=3.

Size of fruit pistil scar on shell: small, descriptor=3.

Hairiness of top of fruit: weak to medium.

Curvature of nut basal scar: plane.

Double kernels: absent.

Kernel shape: globular.

Lateral groove in kernel: absent.

Skin of kernel: descriptor=5 (medium corky).

Nut yield (kg per tree): total 29.39 kg per tree in first trial, 23.46 kg per tree in second trial.

Storability of fruits: excellent, similar to OSU releases and check cultivars

Disease/Pest Resistance:

Plants of 'PollyO' are highly resistant to eastern filbert blight caused by the fungus *Anisogramma anomala* (Peck) E. Müller, although a few small cankers may develop under high disease pressure. Plants of 'PollyO' are resistant to bud mites (*Phytoptus avellanae* Nal.), while plants of 'Tonda Gentile delle Langhe' are highly susceptible, and plants of 'Barcelona' are highly resistant.

Temperature Tolerance:

Plants of 'PollyO' have been observed to tolerate temperatures from −21 to 38° C. in the field in Corvallis, Oreg.

Comparative Data:

Tree Size, Growth Habit, Yield, and Yield Efficiency.

Figure 2:
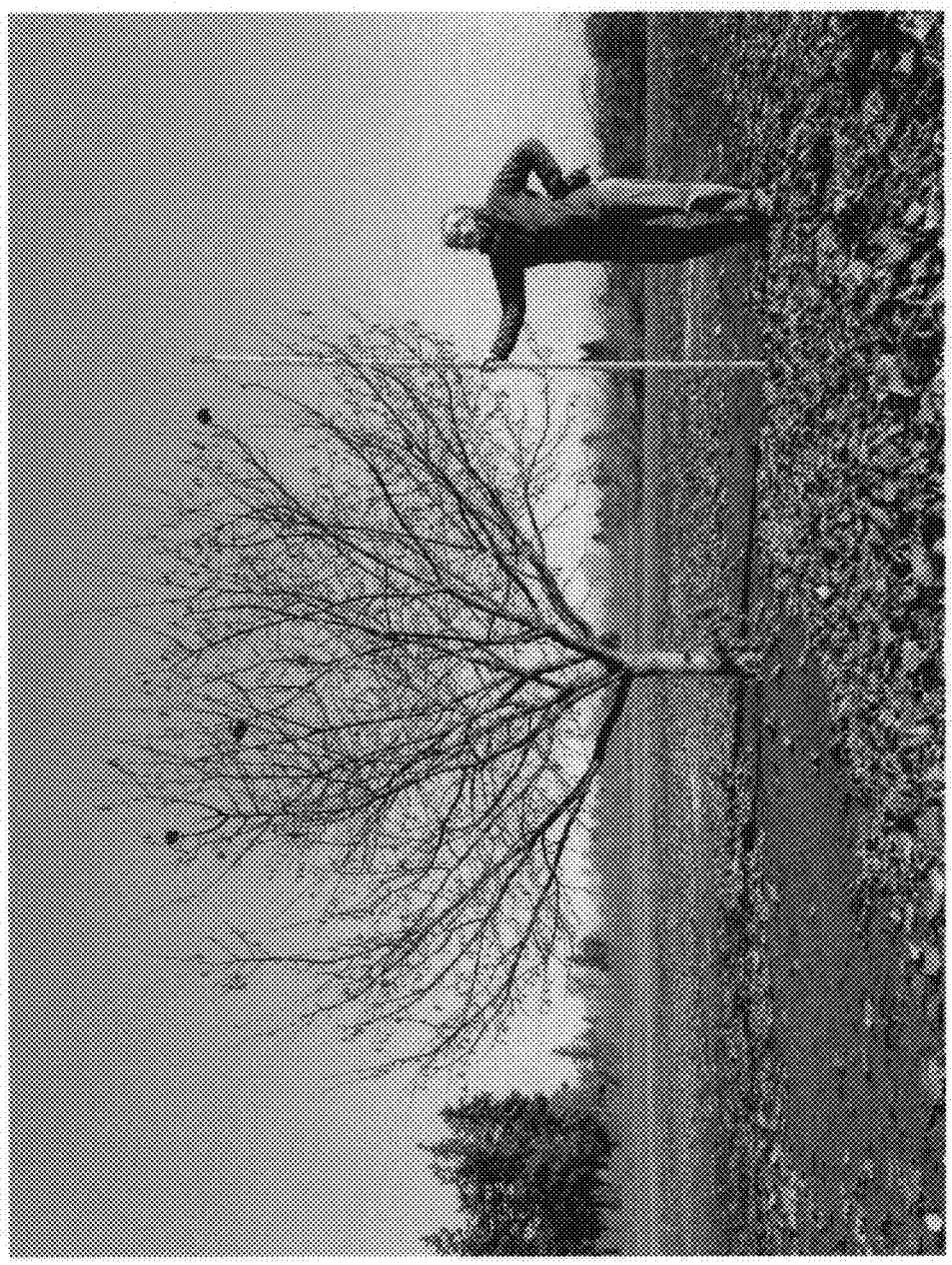
FIG. 2 shows a 'PollyO' (OSU 1108.001) hazelnut tree at the end of the seventh growing season. The pole height is 10 feet.

Tree sizes in the two trials were estimated by measuring trunk circumference 30 cm above the soil line, at the end of the $7^{th}$ growing season (December 2016 and November 2017, respectively). Trunk cross-sectional area (TCA) was calculated from trunk circumference. In the first trial, TCA of 'PollyO' (OSU 1108.001) was 118 $cm^2$ or 126% of 'Jefferson' and 91% of 'Barcelona' in the adjacent trial of EFB-susceptible selections. In the second trial, TCA of 'PollyO' (OSU 1108.001) was 117.6 $cm^2$, or 146% of 'Jefferson'. In previous trials, TCA of 'Jefferson' has been about 65-70% of the vigorous standard 'Barcelona', a size that pleases Oregon growers. Trees of 'PollyO' (OSU 1108.001) are vigorous, and their globose growth habit (FIG. 2) should be grower-friendly (easy to manage).

In the first trial, mean total nut yield (2013-16) of 'PollyO' (OSU 1108.001) was 29.4 kg compared to 24.3 kg for 'Jefferson' (Tables 1-2). Yield efficiency, the ratio of yield to TCA, adjusts yield for differences in tree size. Yield efficiency of 'PollyO' (OSU 1108.001) was 0.251 kg/$cm^2$ which is not significantly different from 'Jefferson' (0.261 kg/$cm^2$). In the second trial, mean total nut yield was 23.46 kg for 'PollyO' (OSU 1108.001) which is significantly higher than the 16.91 kg for 'Jefferson' (Tables 3-4). Yield efficiency was 0.201 kg/$cm^2$ for 'PollyO' (OSU 1108.001) which is not significantly different from 'Jefferson' (0.210 kg/$cm^2$).

TABLE 1

Nut yield of 'PollyO' (OSU 1108.001) in comparison with other hazelnut cultivars and selections in the first trial, planted in 2010. Randomized complete block design with four blocks and a single tree of each selection in each block.

| | | Nut Yield per tree (kg) | | | | |
|---|---|---|---|---|---|---|
| Selection | CvNo | 2013 | 2014 | 2015 | 2016 | Total |
| EFB-resistant selections | | | | | | |
| 1069.092 | 1 | 1.06 | 2.76 | 3.54 | 7.93 | 15.29 |
| 1072.105 | 2 | 0.98 | 3.14 | 4.65 | 8.39 | 17.14 |
| 1081.101 | 3 | 1.03 | 4.02 | 4.23 | 7.45 | 16.73 |
| 1084.075 | 4 | 1.07 | 2.27 | 4.58 | 5.81 | 13.73 |
| 1085.066 | 5 | 2.57 | 3.97 | 6.24 | 8.47 | 21.25 |

TABLE 1-continued

Nut yield of 'PollyO' (OSU 1108.001) in comparison with other hazelnut cultivars and selections in the first trial, planted in 2010. Randomized complete block design with four blocks and a single tree of each selection in each block.

| | | Nut Yield per tree (kg) | | | | |
|---|---|---|---|---|---|---|
| Selection | CvNo | 2013 | 2014 | 2015 | 2016 | Total |
| 1086.145 | 6 | 1.45 | 4.97 | 5.77 | 10.64 | 22.82 |
| 1102.032 | 7 | 1.02 | 3.86 | 3.83 | 8.29 | 17.00 |
| 1102.069 | 8 | 1.50 | 3.48 | 4.84 | 7.48 | 17.30 |
| 1108.001 | 9 | 2.69 | 7.21 | 8.07 | 11.42 | 29.39 |
| 1119.081 | 10 | 2.59 | 4.88 | 5.46 | 7.84 | 20.77 |
| 1130.006 | 11 | 1.59 | 4.44 | 4.36 | 8.22 | 18.61 |
| 1130.009 | 12 | 0.87 | 1.76 | 3.20 | 4.62 | 10.44 |
| 1131.072 | 13 | 2.39 | 4.70 | 3.60 | 10.05 | 20.74 |
| Gamma | 14 | 0.82 | 3.45 | 3.89 | 7.10 | 15.26 |
| Jefferson | 15 | 3.44 | 5.37 | 4.59 | 10.87 | 24.26 |
| Yamhill | 16 | 1.93 | 5.80 | 6.85 | 11.89 | 26.47 |
| LSD (0.05) | | 0.56 | 0.97 | 1.13 | 2.55 | 3.83 |

TABLE 2

Trunk cross-sectional area (TCA), yield efficiency, and relative tree size of 'PollyO' (OSU 1108.001) in comparison with other hazelnut cultivars and selections in the first trial, planted in 2010. Randomized complete block design with four blocks and a single tree of each selection in each block.

| | | TCA | Yield Efficiency | Relative tree size (%) | |
|---|---|---|---|---|---|
| Selection | CvNo | ($cm^2$) | ($kg/cm^2$) | To Barcelona | To Jefferson |
| EFB-resistant selections | | | | | |
| 1069.092 | 1 | 143.76 | 0.107 | 110 | 154 |
| 1072.105 | 2 | 131.08 | 0.130 | 101 | 141 |
| 1081.101 | 3 | 85.81 | 0.194 | 66 | 92 |
| 1084.075 | 4 | 82.73 | 0.166 | 64 | 89 |
| 1085.066 | 5 | 87.55 | 0.248 | 67 | 94 |
| 1086.145 | 6 | 122.81 | 0.186 | 94 | 132 |
| 1102.032 | 7 | 100.57 | 0.169 | 77 | 108 |
| 1102.069 | 8 | 90.98 | 0.190 | 70 | 98 |
| 1108.001 | 9 | 117.78 | 0.251 | 91 | 126 |
| 1119.081 | 10 | 64.16 | 0.327 | 49 | 69 |
| 1130.006 | 11 | 129.45 | 0.147 | 100 | 139 |
| 1130.009 | 12 | 88.23 | 0.119 | 68 | 95 |
| 1131.072 | 13 | 110.57 | 0.188 | 85 | 119 |
| Gamma | 14 | 108.68 | 0.141 | 84 | 117 |
| Jefferson | 15 | 93.15 | 0.261 | 72 | 100 |
| Yamhill | 16 | 79.32 | 0.334 | 61 | 85 |
| LSD (0.05) | | 16.00 | 0.044 | | |

TABLE 3

Nut yield of 'PollyO' (OSU 1108.001) in comparison with other hazelnut cultivars and selections in the second trial, planted in 2011. Randomized complete block design with seven blocks and a single tree of each selection in each block.

| | | Nut yield (kg/tree) | | | | |
|---|---|---|---|---|---|---|
| Selection | n | 2013 | 2014 | 2015 | 2016 | 2017 |
| OSU 992.022 | 7 | 0.22 | 1.89 | 3.18 | 7.43 | 5.32 |
| OSU 1014.058 | 7 | 0.56 | 2.35 | 3.21 | 5.49 | 5.60 |
| OSU 1018.001 | 7 | 0.23 | 1.10 | 2.65 | 5.82 | 5.48 |
| OSU 1086.053 | 7 | 0.38 | 1.59 | 2.59 | 6.57 | 4.39 |
| OSU 1086.145 | 7 | 0.17 | 2.37 | 3.77 | 8.22 | 6.39 |
| OSU 1102.069 | 7 | 0.33 | 0.99 | 2.98 | 4.35 | 3.70 |
| OSU 1108.001 | 7 | 0.18 | 2.24 | 4.48 | 9.99 | 6.57 |

TABLE 3-continued

Nut yield of 'PollyO' (OSU 1108.001) in comparison with other hazelnut cultivars and selections in the second trial, planted in 2011. Randomized complete block design with seven blocks and a single tree of each selection in each block.

| | | Nut yield (kg/tree) | | | | |
|---|---|---|---|---|---|---|
| Selection | n | 2013 | 2014 | 2015 | 2016 | 2017 |
| OSU 1108.042 | 7 | 0.19 | 1.57 | 4.12 | 8.73 | 4.73 |
| OSU 1130.006 | 6 | 0.18 | 0.49 | 1.68 | 4.66 | 4.70 |
| OSU 1130.009 | 7 | 0.18 | 0.79 | 1.28 | 2.87 | 3.04 |
| OSU 1131.072 | 7 | 0.34 | 2.24 | 3.00 | 6.36 | 5.87 |
| OSU 1136.051 | 7 | 0.67 | 2.42 | 2.78 | 5.28 | 4.02 |
| OSU 1152.063 | 7 | 0.17 | 1.97 | 3.71 | 5.38 | 5.37 |
| OSU 1153.052 | 6 | 0.21 | 0.88 | 2.94 | 7.03 | 4.96 |
| OSU 1154.027 | 7 | 0.13 | 2.21 | 4.62 | 6.58 | 6.95 |
| Jefferson | 7 | 0.40 | 2.59 | 3.01 | 5.94 | 4.98 |
| Yamhill | 7 | 0.43 | 2.44 | 4.19 | 8.14 | 6.50 |
| $LSD_{(.05)}$ | | 0.14 | 0.43 | 0.66 | 1.10 | 0.97 |

TABLE 4

TCA and yield efficiency of 'PollyO' (OSU 1108.001) in comparison with other hazelnut cultivars and selections in the second trial, planted in 2011. Randomized complete block design with seven blocks and a single tree of each selection in each block.

| | | | Total field-run yield (kg/tree)[y] | | Yield efficiency (total kg/cm2) | |
|---|---|---|---|---|---|---|
| Selection | n | TCA ($cm^2$)[z] | Nut | Kernel | Nut | Kernel |
| EFB-resistant selections | | | | | | |
| OSU 992.022 | 7 | 105.4 | 18.04 | 8.32 | .171 | .079 |
| OSU 1014.058 | 7 | 93.9 | 17.21 | 7.90 | .186 | .085 |
| OSU 1018.001 | 7 | 80.6 | 15.27 | 7.11 | .190 | .088 |
| OSU 1086.053 | 7 | 105.4 | 15.52 | 6.76 | .148 | .066 |
| OSU 1086.145 | 7 | 130.6 | 20.91 | 9.72 | .160 | .075 |
| OSU 1102.069 | 7 | 78.5 | 12.34 | 5.85 | .156 | .074 |
| OSU 1108.001 | 7 | 117.6 | 23.46 | 11.26 | .201 | .097 |
| OSU 1108.042 | 7 | 108.6 | 19.34 | 8.51 | .179 | .079 |
| OSU 1130.006 | 6 | 107.5 | 11.71 | 5.36 | .110 | .050 |
| OSU 1130.009 | 7 | 73.9 | 8.15 | 3.74 | .110 | .050 |
| OSU 1131.072 | 7 | 121.5 | 17.80 | 8.31 | .147 | .069 |
| OSU 1136.051 | 7 | 70.1 | 15.18 | 6.60 | .217 | .095 |
| OSU 1152.063 | 7 | 103.4 | 16.60 | 7.60 | .162 | .077 |
| OSU 1153.052 | 6 | 106.3 | 16.02 | 7.46 | .151 | .070 |
| OSU 1154.027 | 7 | 111.3 | 20.49 | 9.47 | .184 | .084 |
| Jefferson | 7 | 80.3 | 16.91 | 7.53 | .210 | .094 |
| Yamhill | 7 | 84.4 | 21.69 | 9.89 | .258 | .118 |
| LSD (.05) | | 11.0 | 2.10 | 0.98 | .021 | .009 |

[z]TCA = Trunk cross-sectional area calculated from trunk circumference measured 30 cm above the soil line in November 2017;
[y]Cumulative kernel yield and yield efficiency are based on field-run samples, with defects not removed.

Nut and Kernel Defects.

Samples of 100 nuts were cracked from each tree in each year. No problems were noted in either trial, although many differences among selections in the trials lack statistical significance because of the small number of replications. In both trials (Tables 3-5), 'PollyO' (OSU 1108.001) showed a high percentage of good nuts, and low percentages of blanks, brown stain, poorly filled nuts, twins, and kernels with black tips. In the first trial, the frequency of moldy kernels (2.56%) was similar to 'Yamhill' and lower than 'Jefferson'. In the second trial, the frequency of moldy kernels (3.4%) was similar to 'Jefferson' (4.3%). Percent kernel (the ratio of kernel weight to nut weight) for 'PollyO' (OSU 1108.001) was 47.9% in the first trial based on well-filled nuts, and 46.9% in the second trial based on field-run nuts. In the same trials, the percent kernel for 'Jefferson' was 45.7% and 44.4%, respectively. Yields of kernels per acre would be high for 'PollyO' (OSU 1108.001). In the two trials, nut yields of 'PollyO' (OSU 1108.001) were consistently good and the nuts consistently well-filled. In contrast, 'Yamhill' trees occasionally set very heavy nut crops, and the nuts can be so poorly filled that the kernels are not marketable. This was the case for 'Yamhill' in the final year of the first trial, when 27% of the nuts were poorly filled.

TABLE 5

Nut weight, kernel weight, and percent kernel of 'PolyO' (OSU 1108.001) in comparison with other hazelnut cultivars and selections in the first trial, planted in 2010. Randomized complete block design with four blocks and a single tree of each selection in each block.

| Selection | CvNo | Nut Weight (g) | Kernel Weight (g) | Percent Kernel |
|---|---|---|---|---|
| 1069.092 | 1 | 3.20 | 1.47 | 45.93 |
| 1072.105 | 2 | 2.73 | 1.22 | 44.65 |
| 1081.101 | 3 | 3.01 | 1.34 | 44.58 |
| 1084.075 | 4 | 2.53 | 1.22 | 48.42 |
| 1085.066 | 5 | 3.40 | 1.45 | 42.70 |
| 1086.145 | 6 | 2.60 | 1.26 | 48.60 |
| 1102.032 | 7 | 3.08 | 1.46 | 47.48 |
| 1102.069 | 8 | 2.94 | 1.46 | 49.64 |
| 1108.001 | 9 | 2.88 | 1.38 | 47.90 |
| 1119.081 | 10 | 3.09 | 1.37 | 44.36 |
| 1130.006 | 11 | 2.56 | 1.19 | 46.57 |
| 1130.009 | 12 | 2.57 | 1.24 | 48.00 |
| 1131.072 | 13 | 2.99 | 1.43 | 47.73 |
| Gamma | 14 | 2.48 | 1.29 | 51.90 |
| Jefferson | 15 | 3.65 | 1.67 | 45.70 |
| Yamhill | 16 | 2.32 | 1.10 | 47.11 |
| LSD (0.05) | | 0.16 | 0.07 | 0.94 |

TABLE 6

Ratings for fiber, blanching (pellicle removal), and bud mite susceptibility of 'PollyO'(OSU 1108.001) in comparison with other hazelnut cultivars and selection sin the first trial, planted in 2010. Randomized complete block design with four blocks and a single tree of each selection in each block.

| Selection | CvNo | Fiber Rating (1-4) | Blanching Rating (1-7) | Bud Mite Rating (1-5) |
|---|---|---|---|---|
| 1069.092 | 1 | 2.66 | 5.59 | 1.13 |
| 1072.105 | 2 | 1.38 | 4.56 | 2.42 |
| 1081.101 | 3 | 2.69 | 4.34 | 2.49 |
| 1084.075 | 4 | 2.47 | 4.28 | 1.02 |
| 1085.066 | 5 | 1.44 | 2.97 | 1.94 |
| 1086.145 | 6 | 1.61 | 4.03 | 2.35 |
| 1102.032 | 7 | 2.39 | 4.96 | 1.91 |
| 1102.069 | 8 | 1.25 | 4.31 | 1.04 |
| 1108.001 | 9 | 3.28 | 3.66 | 1.15 |
| 1119.081 | 10 | 2.72 | 3.28 | 1.97 |
| 1130.006 | 11 | 2.97 | 4.00 | 2.88 |
| 1130.009 | 12 | 2.88 | 3.69 | 2.25 |
| 1131.072 | 13 | 3.06 | 3.94 | 1.56 |
| Gamma | 14 | 3.09 | 6.28 | 2.96 |
| Jefferson | 15 | 3.00 | 4.34 | 1.34 |
| Yamhill | 16 | 1.25 | 5.00 | 1.10 |
| LSD (0.05) | | 0.26 | 0.29 | 0.26 |

Fiber amount on the pellicle rated from 1 (no fiber) to 4 (heavy fiber).
Blanching after roasting at 275 F. for 15 min rated from 1 (complete pellicle removal) to 7 (no pellicle removal).
Bud mite: incidence of blasted bud rated in 5 years in December on a scale of 1.

TABLE 7

Frequency of good nuts, and of nut and kernel defects in 'PollyO' (OSU 1108.001) and other hazelnut cultivars and selections in the first trial, planted in 2010.

| | | Frequency (%) | | | |
|---|---|---|---|---|---|
| Selection | CvNo | Good | Blank | Brown Stain | Moldy |
| 1069.092 | 1 | 81.62 | 3.26 | 0.56 | 4.12 |
| 1072.105 | 2 | 83.62 | 2.32 | 2.06 | 4.32 |
| 1081.101 | 3 | 80.18 | 7.18 | 0.18 | 6.44 |
| 1084.075 | 4 | 80.88 | 3.06 | 0.18 | 6.18 |
| 1085.066 | 5 | 78.50 | 3.38 | 0.32 | 4.94 |
| 1086.145 | 6 | 73.86 | 9.00 | 0.30 | 9.02 |
| 1102.032 | 7 | 83.02 | 4.14 | 0.36 | 4.08 |
| 1102.069 | 8 | 74.44 | 7.50 | 1.00 | 6.26 |
| 1108.001 | 9 | 83.38 | 4.00 | 0.06 | 2.56 |
| 1119.081 | 10 | 75.32 | 4.26 | 0.18 | 6.12 |
| 1130.006 | 11 | 84.32 | 5.06 | 0.44 | 4.38 |
| 1130.009 | 12 | 80.32 | 8.32 | 0.26 | 5.12 |
| 1131.072 | 13 | 78.68 | 7.38 | 1.26 | 3.44 |
| Gamma | 14 | 75.38 | 7.62 | 1.26 | 5.38 |
| Jefferson | 15 | 73.68 | 4.00 | 0.18 | 6.12 |
| Yamhill | 16 | 74.18 | 2.18 | 0.26 | 2.68 |
| LSD (0.05) | | 6.80 | 2.75 | 1.18 | 2.38 |

TABLE 8

Frequency of nut and kernel defects in 'PollyO' (OSU 1108.001) and other hazelnut cultivars and selections in the first trial, planted in 2010.

| | | Frequency (%) | | | |
|---|---|---|---|---|---|
| Selection | CvNo | Shrivels | Poor Fill | Twins | Black Tips |
| 1069.092 | 1 | 2.18 | 6.44 | 1.76 | 0.38 |
| 1072.105 | 2 | 0.56 | 7.00 | 0.12 | 0.38 |
| 1081.101 | 3 | 0.82 | 3.18 | 1.18 | 1.06 |
| 1084.075 | 4 | 0.68 | 8.82 | 1.18 | 0.26 |
| 1085.066 | 5 | 1.06 | 11.32 | 0.38 | 0.88 |
| 1086.145 | 6 | 1.30 | 4.94 | 0.94 | 1.62 |
| 1102.032 | 7 | 0.88 | 6.00 | 2.00 | 0.16 |
| 1102.069 | 8 | 1.18 | 6.80 | 4.00 | 0.18 |
| 1108.001 | 9 | 1.50 | 8.62 | 0.12 | 0.06 |
| 1119.081 | 10 | 3.06 | 11.32 | 0.76 | 0.12 |
| 1130.006 | 11 | 0.68 | 4.06 | 0.12 | 1.12 |
| 1130.009 | 12 | 0.38 | 5.68 | 0.26 | 0.26 |
| 1131.072 | 13 | 1.82 | 7.12 | 1.18 | 0.26 |
| Gamma | 14 | 0.88 | 8.32 | 0.12 | 0.26 |
| Jefferson | 15 | 0.56 | 13.26 | 0.88 | 2.12 |
| Yamhill | 16 | 3.88 | 16.76 | 0.06 | 0.12 |
| LSD (0.05) | | 1.83 | 5.12 | 0.88 | 0.66 |

TABLE 9

Nut weight, kernel weight, and percent kernel in 'PollyO' (OSU 1108.001) and other hazelnut cultivars and selections in the second trial, planted in 2011.

| | | Frequency (%) | | |
|---|---|---|---|---|
| Selection[z] | n | Nut weight (g) | Kernel weight (g) | Percent Kernel |
| OSU 992.022 | 7 | 2.57 | 1.18 | 46.0 |
| OSU 1014.058 | 7 | 2.31 | 1.05 | 45.6 |
| OSU 1018.001 | 7 | 2.35 | 1.07 | 45.4 |
| OSU 1086.053 | 7 | 2.58 | 1.11 | 43.2 |
| OSU 1086.145 | 7 | 2.38 | 1.12 | 46.7 |
| OSU 1102.069 | 7 | 2.80 | 1.32 | 47.0 |
| OSU 1108.001 | 7 | 2.75 | 1.29 | 46.9 |
| OSU 1108.042 | 7 | 2.57 | 1.12 | 43.5 |
| OSU 1130.006 | 6 | 2.39 | 1.08 | 45.0 |

TABLE 9-continued

Nut weight, kernel weight, and percent kernel in 'PollyO' (OSU 1108.001) and other hazelnut cultivars and selections in the second trial, planted in 2011.

| | | Frequency (%) | | |
|---|---|---|---|---|
| Selection[z] | n | Nut weight (g) | Kernel weight (g) | Percent Kernel |
| OSU 1130.009 | 7 | 2.40 | 1.08 | 45.2 |
| OSU 1131.072 | 7 | 2.86 | 1.31 | 45.7 |
| OSU 1136.051 | 7 | 2.69 | 1.16 | 43.2 |
| OSU 1152.063 | 7 | 2.38 | 1.10 | 46.1 |
| OSU 1153.052 | 6 | 2.68 | 1.22 | 45.8 |
| OSU 1154.027 | 7 | 2.34 | 1.06 | 45.4 |
| Jefferson | 7 | 3.45 | 1.53 | 44.4 |
| Yamhill | 7 | 2.28 | 1.04 | 45.8 |
| $LSD_{(.05)}$ | | 0.15 | 0.03 | 0.8 |

[z]Data from seven replications of each selection (2013-17) unless otherwise noted, with a single tree of each selection in each block.

TABLE 10

Frequency of good nuts and of nut and kernel defects in 'PollyO' (OSU 1108.001) and other hazelnut cultivars and selections in the second trial, planted in 2011.

| Selection[z] | n | Blanch | Good Nuts | Blanks (Frequency %) |
|---|---|---|---|---|
| OSU 992.022 | 7 | 4.1 | 89.3 | 4.8 |
| OSU 1014.058 | 7 | 4.7 | 96.0 | 1.2 |
| OSU 1018.001 | 7 | 3.9 | 90.6 | 4.5 |
| OSU 1086.053 | 7 | 3.7 | 89.1 | 6.1 |
| OSU 1086.145 | 7 | 4.4 | 87.8 | 6.0 |
| OSU 1102.069 | 7 | 4.1 | 85.9 | 4.1 |
| OSU 1108.001 | 7 | 3.5 | 93.0 | 2.5 |
| OSU 1108.042 | 7 | 4.6 | 91.8 | 3.3 |
| OSU 1130.006 | 6 | 4.5 | 91.6 | 3.5 |
| OSU 1130.009 | 7 | 3.9 | 89.8 | 5.1 |
| OSU 1131.072 | 7 | 4.2 | 90.5 | 3.8 |
| OSU 1136.051 | 7 | 3.4 | 86.5 | 3.6 |
| OSU 1152.063 | 7 | 4.2 | 92.7 | 4.7 |
| OSU 1153.052 | 6 | 3.9 | 89.9 | 2.9 |
| OSU 1154.027 | 7 | 4.9 | 95.0 | 2.1 |
| Jefferson | 7 | 4.6 | 89.0 | 3.9 |
| Yamhill | 7 | 5.1 | 95.6 | 1.6 |
| LSD (.05) | | 0.3 | 2.2 | 1.4 |

[z]Data from seven replications of each selection (2013-17) unless otherwise noted, with a single tree of each selection in each block.

TABLE 11

Frequency of nut and kernel defects in 'PollyO' (OSU 1108.001) and other hazelnut cultivars and selections in the second trial, planted in 2011.

| | | Frequency (%) | | | | | |
|---|---|---|---|---|---|---|---|
| Selection[z] | n | Brown Stain | Mold | Shrivel | Poor Fill | Twin | Black Tip |
| OSU 992.022 | 7 | 0.1 | 4.4 | 0.7 | 0.4 | 0.2 | 0.2 |
| OSU 1014.058 | 7 | 0.0 | 1.9 | 0.4 | 0.1 | 0.2 | 0.2 |
| OSU 1018.001 | 7 | 0.1 | 3.3 | 0.1 | 0.2 | 0.9 | 0.3 |
| OSU 1086.053 | 7 | 0.0 | 4.3 | 0.2 | 0.2 | 0.2 | 0.1 |
| OSU 1086.145 | 7 | 0.0 | 3.6 | 0.8 | 0.6 | 0.6 | 0.7 |
| OSU 1102.069 | 7 | 0.3 | 4.1 | 0.7 | 0.4 | 3.6 | 0.8 |
| OSU 1108.001 | 7 | 0.1 | 3.4 | 0.3 | 0.3 | 0.1 | 0.4 |
| OSU 1108.042 | 7 | 0.1 | 2.9 | 0.5 | 0.9 | 0.3 | 0.2 |
| OSU 1130.006 | 6 | 0.1 | 2.6 | 0.2 | 0.3 | 0.1 | 1.7 |
| OSU 1130.009 | 7 | 0.2 | 4.0 | 0.4 | 0.2 | 0.0 | 0.2 |
| OSU 1131.072 | 7 | 0.2 | 1.9 | 0.8 | 1.0 | 1.7 | 0.1 |
| OSU 1136.051 | 7 | 0.3 | 4.5 | 2.6 | 0.4 | 1.4 | 0.4 |
| OSU 1152.063 | 7 | 0.7 | 0.7 | 0.1 | 0.6 | 0.1 | 0.4 |

TABLE 11-continued

Frequency of nut and kernel defects in 'PollyO' (OSU 1108.001) and other hazelnut cultivars and selections in the second trial, planted in 2011.

| | | Frequency (%) | | | | | |
|---|---|---|---|---|---|---|---|
| Selection[z] | n | Brown Stain | Mold | Shrivel | Poor Fill | Twin | Black Tip |
| OSU 1153.052 | 6 | 0.4 | 5.2 | 0.5 | 0.3 | 0.2 | 0.8 |
| OSU 1154.027 | 7 | 0.1 | 1.5 | 0.5 | 0.1 | 0.5 | 0.2 |
| Jefferson | 7 | 0.1 | 4.3 | 0.4 | 0.0 | 0.6 | 1.7 |
| Yamhill | 7 | 0.1 | 1.7 | 0.7 | 0.1 | 0.1 | 0.1 |
| LSD (.05) | | 0.3 | 1.1 | 0.5 | 0.3 | 0.4 | 0.5 |

[z]Data from seven replications of each selection (2013-17) unless otherwise noted, with a single tree of each selection in each block.

Nut and Kernel Characteristics.

Figure 3:
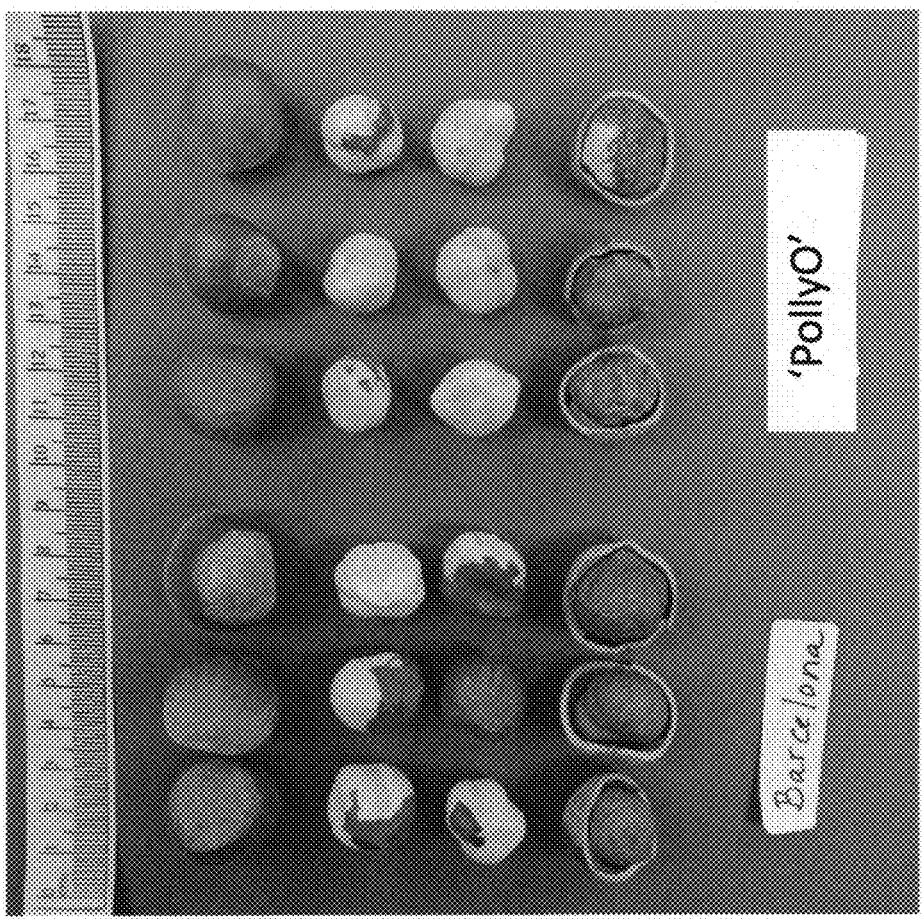
FIG. 3 shows nuts, blanched kernels and raw kernels of 'Barcelona' (left) and 'PollyO' (OSU 1108.001) (right).

'PollyO' can be used for the blanched kernel market as a companion for 'Wepster' and 'McDonald', and an alternative to 'Yamhill'. The nut shape is nearly round and lends itself well to sizing and cracking (FIG. 3). The shells are thin and easy to crack, and most kernels remain whole when the shell is broken. The kernel size of 'PollyO' is small, similar to 'McDonald' but larger than 'Wepster' and 'Yamhill'. The amount of fiber on the pellicle was rated on a scale of 1 (no fiber) to 4 (heavy fiber). Raw kernels have fibrous pellicles (mean rating 3.3) and thus are not particularly attractive. Pellicle removal (blanching) is rated on a scale of 1 (complete pellicle removal) to 7 (no pellicle removal), with ratings <4.0 being desired. Most of the pellicle on 'PollyO' kernels is removed from the kernels with dry heat in the blanching process (ratings=3.7 and 3.5 in the first and second trials, respectively) which is better than 'Yamhill' (ratings=5.0 and 5.1) and 'Jefferson' (ratings 4.3 and 4.6). Blanching removes about half of the pellicle from 'Barcelona' kernels (FIG. 3). Kernel texture, flavor and aroma were evaluated in September 2016 or 2017. Tasters consider kernel quality to be excellent, and well-suited for use in baked goods and chocolate products.

Nut Maturity Date.

Figure 4:
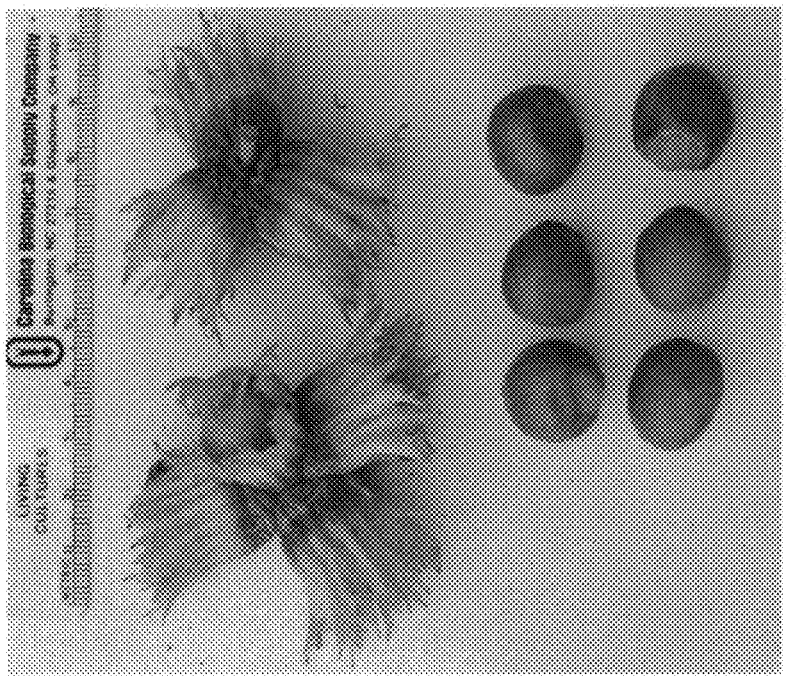
FIG. 4 shows nuts and husks of 'PollyO' hazelnut.
Figure 6:
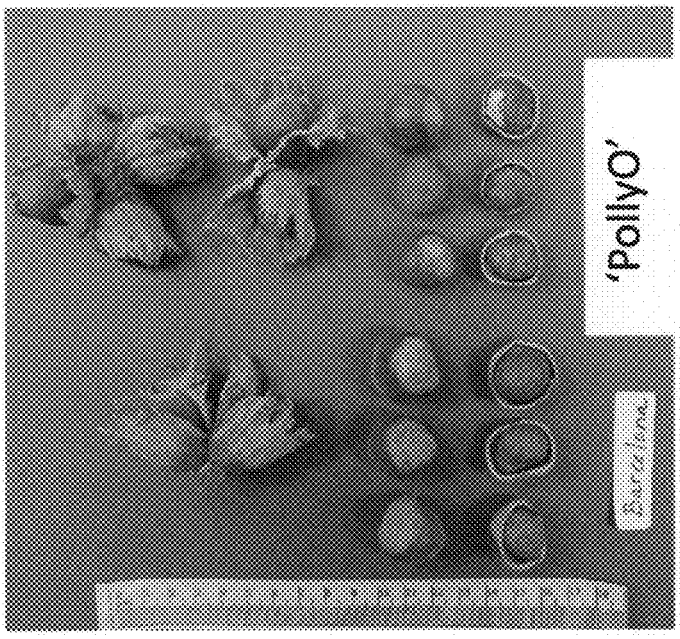
FIGS. 5 and 6 show husks and nuts of 'Barcelona' (left) and 'PollyO' (OSU 1108.001) (right).
Figure 5:
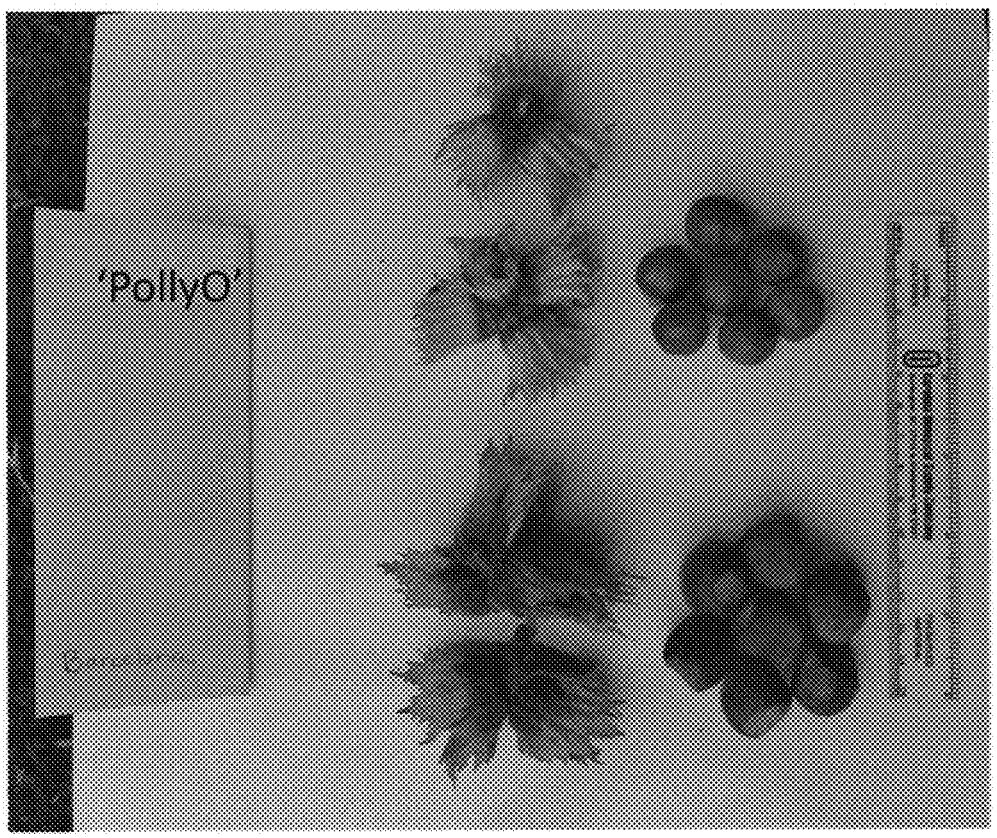
Figure 7:
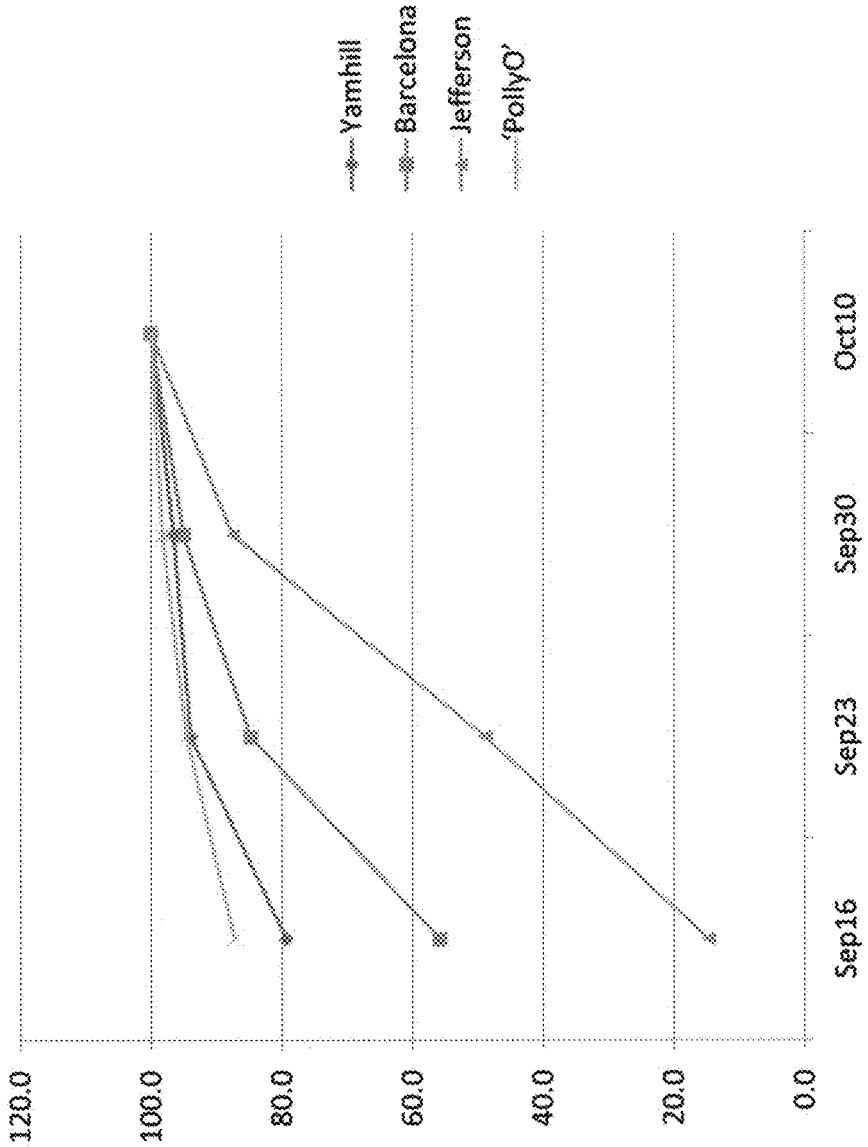
FIG. 7 is a graph showing the cumulative percentage of nuts harvested from the ground on four dates in fall 2016. Nuts were harvested by hand, dried and weighed. Nuts were harvested in the first trial planted in 2010. Nut maturity of 'PollyO' (OSU 1108.001) is a few days earlier than 'Yamhill' or 10-14 days before 'Barcelona'.
Figure 8:
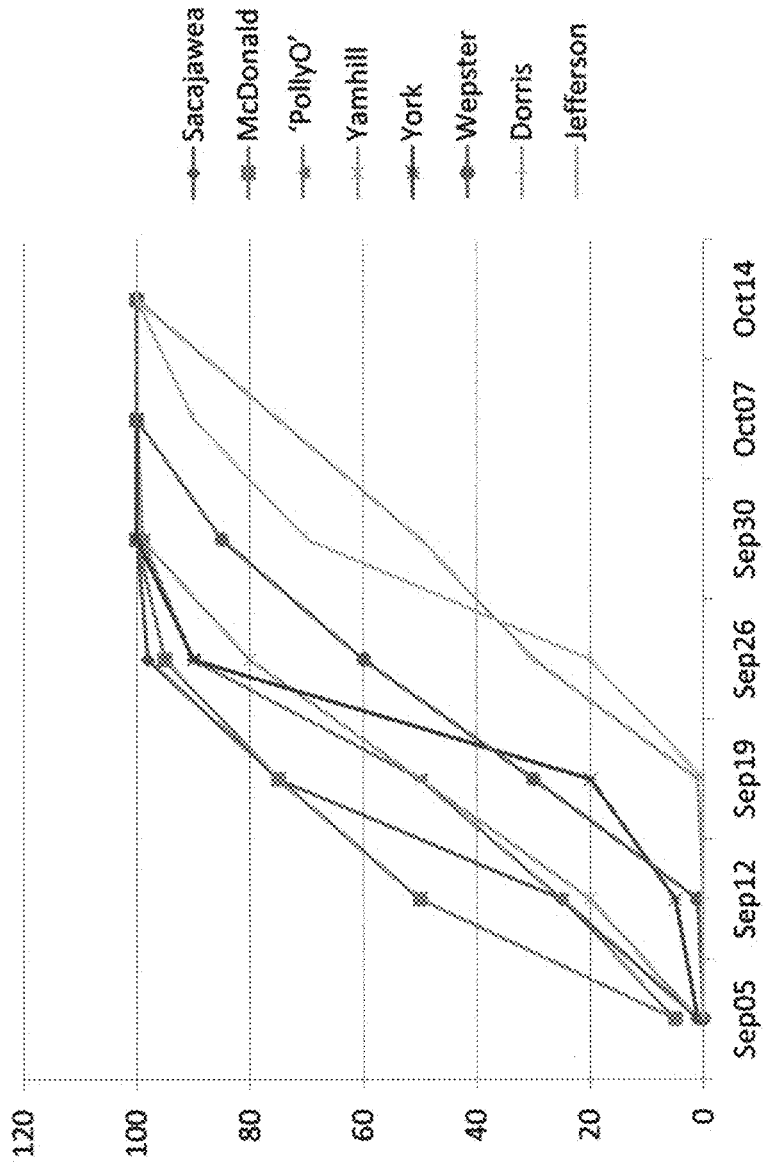
FIG. 8 is a graph showing the estimated percentage of nuts on the ground for eight hazelnut cultivars on seven dates in fall 2017. Reading on the 60% drop line from left to right, the cultivars from earliest to latest nut maturity are: 'McDonald', 'Sacajawea' (unpatented), 'PollyO' (OSU 1108.001), 'Yamhill' (unpatented), 'York', 'Wepster', 'Dorris' and 'Jefferson'. 'McDonald', 'Sacajawea', 'York', 'Wepster' and 'Dorris' were in the guard row planted at the same time as the trial.
Figure 9:
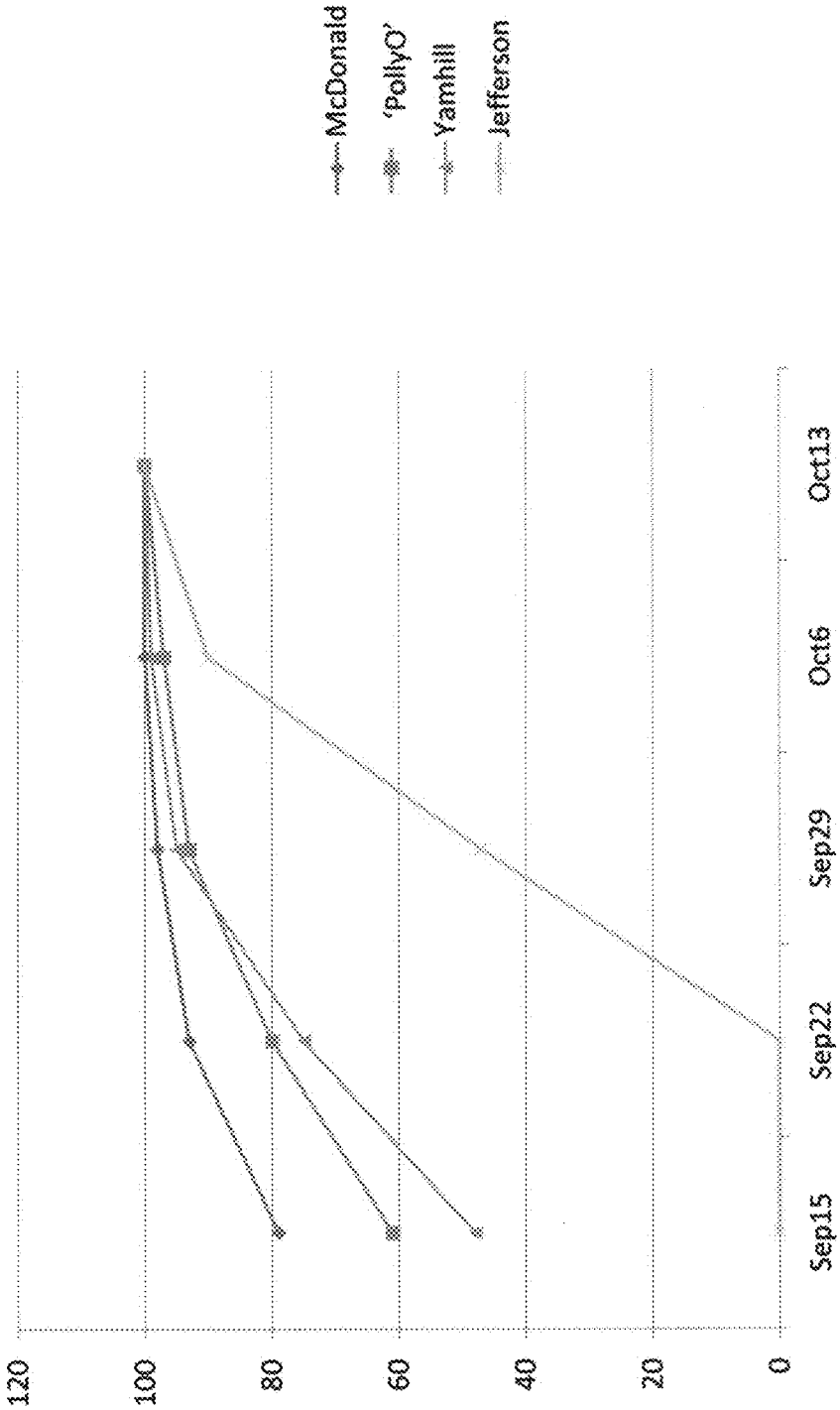
FIG. 9 is a graph showing the cumulative percentage of nuts harvested (based on weight) from the ground for four hazelnut cultivars on five dates in fall 2017. 'McDonald' trees were in the guard row planted at the same time as the trial. Nuts of 'PollyO' (OSU 1108.001) mature after those of 'McDonald' but before those of 'Yamhill'.
Figure 11:
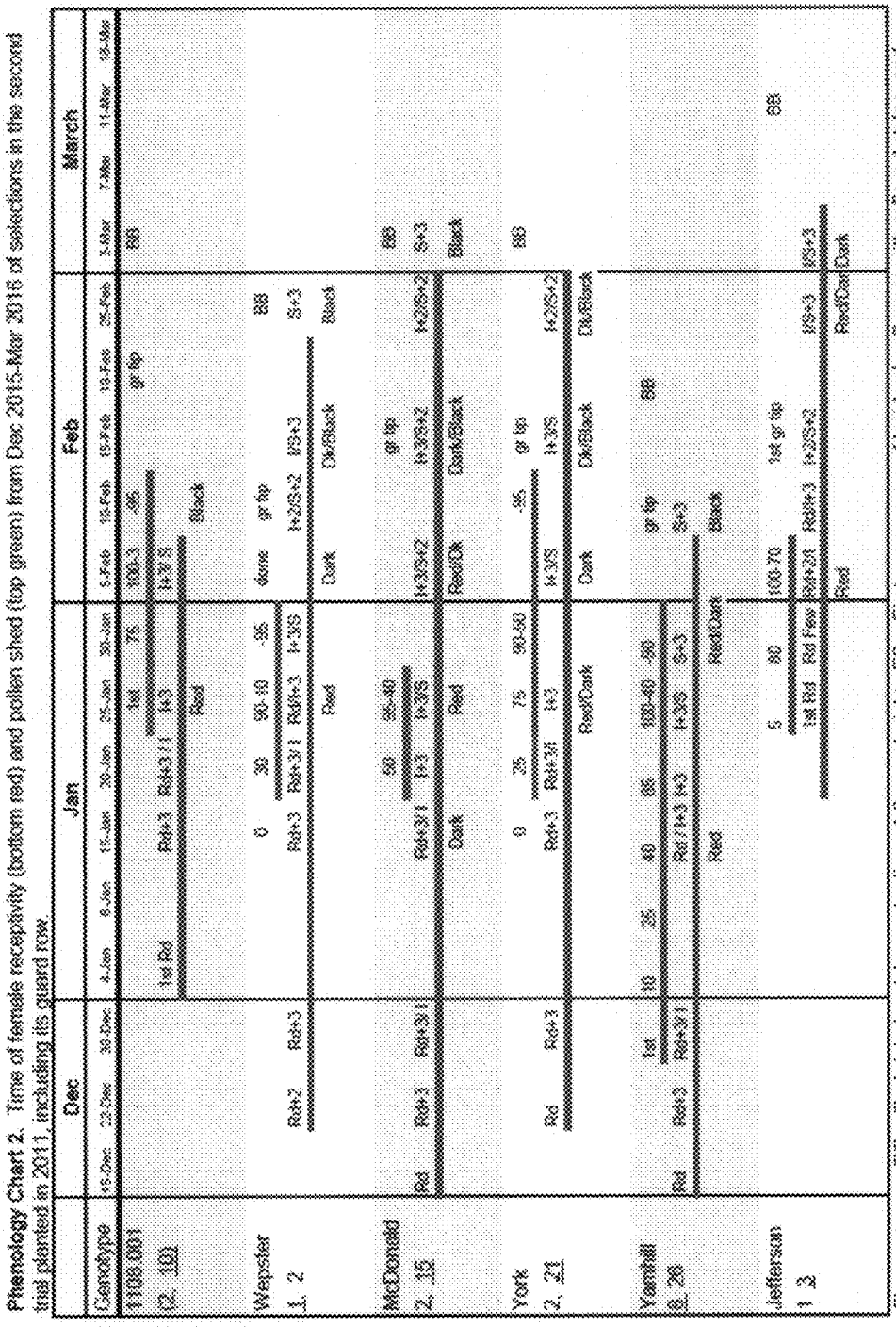
FIG. 11 shows the time of female receptivity (bottom, red) and pollen shed (top, green) of 'PollyO' (OSU 1108.001) and other hazelnut cultivars in a trial planted in 2011 (December 2015-March 2016).
Figure 13:
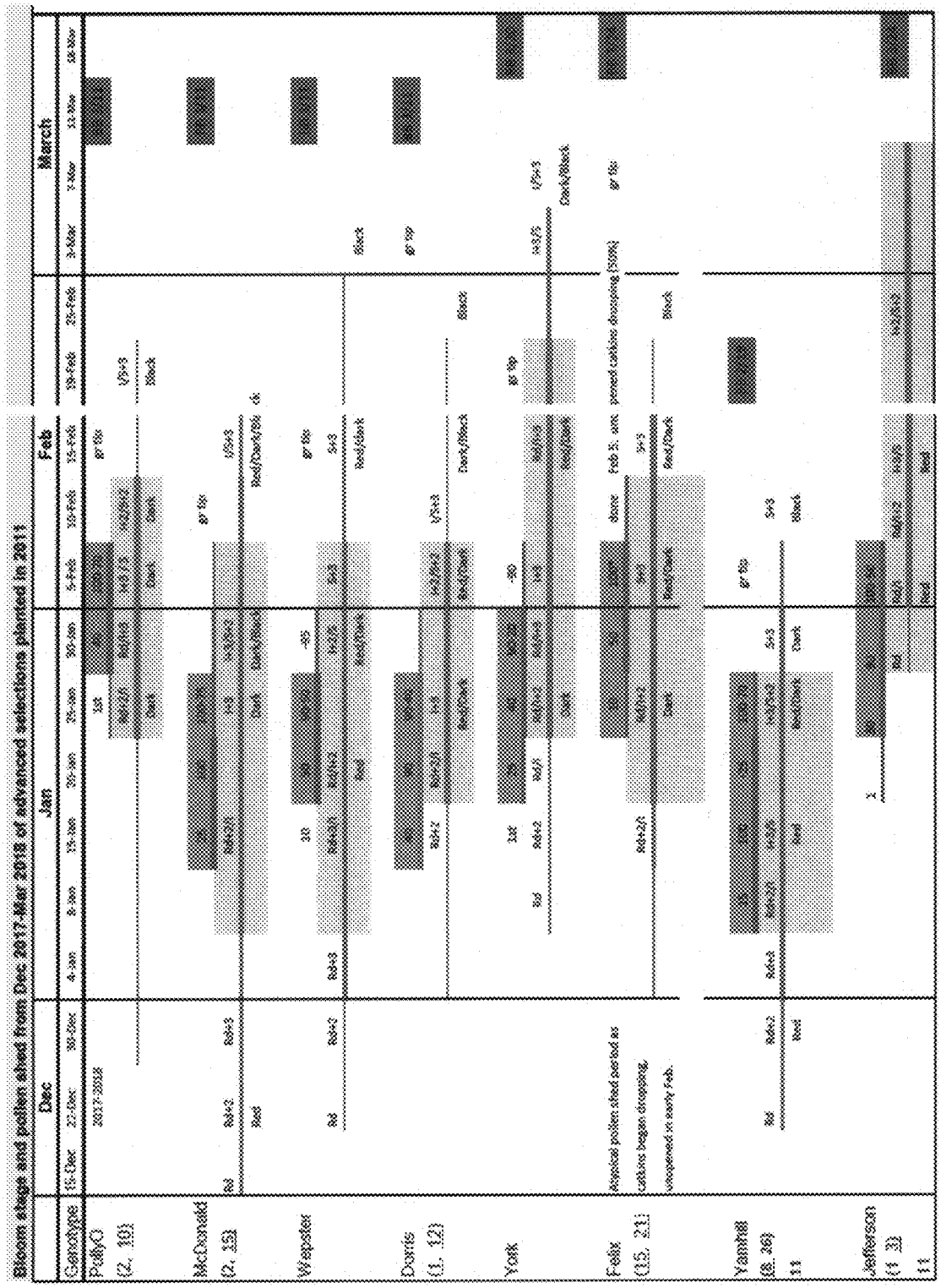
FIG. 13 shows the time of female receptivity (bottom, red) and pollen shed (top, green) of 'PollyO' (OSU 1108.001) and other hazelnut cultivars in a trial planted in 2011 (December 2017-March 2018).
Figure 14:
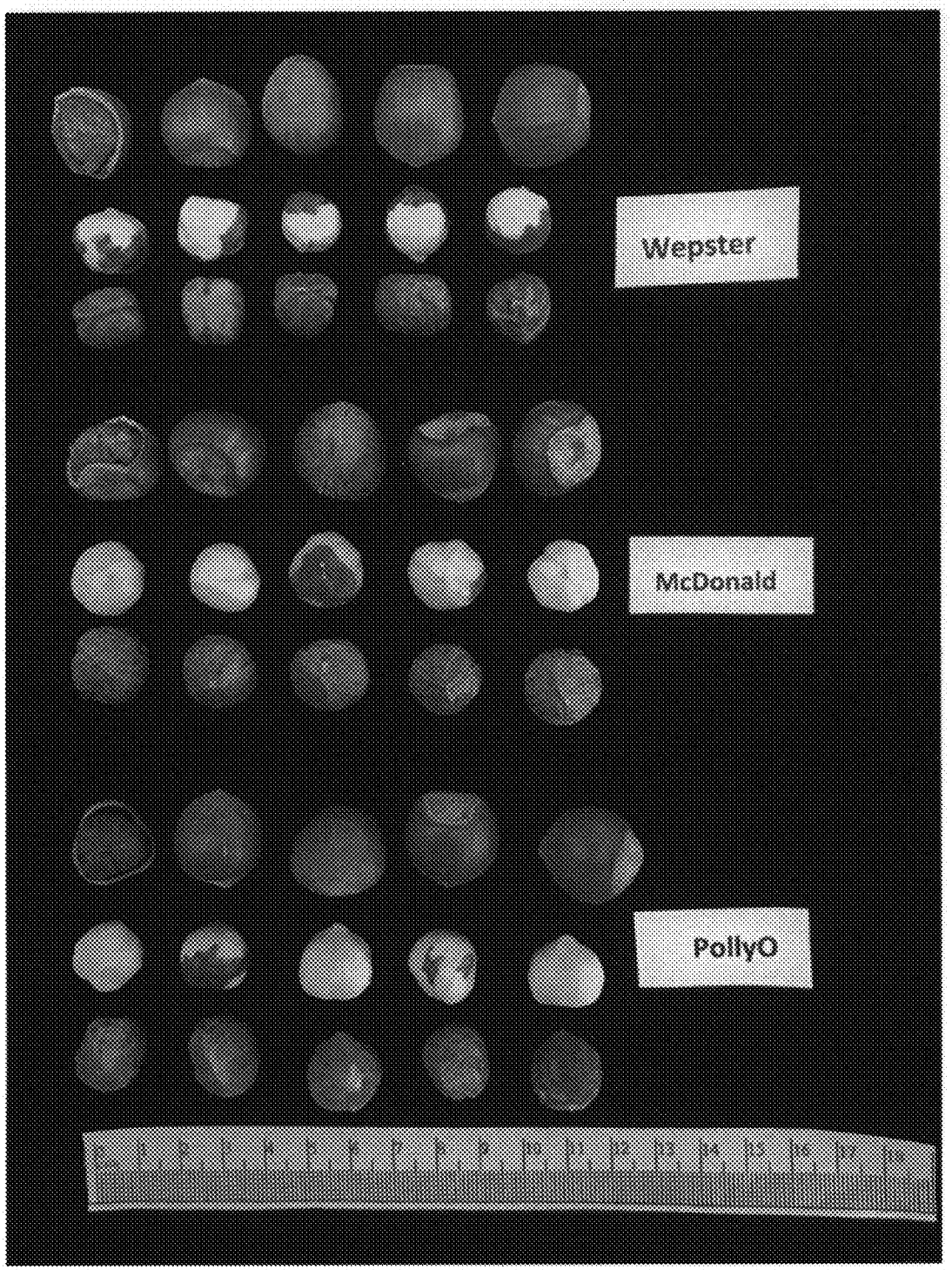
FIG. 14 shows nuts, blanched kernels and raw kernels of 'Wepster', 'McDonald', and 'PollyO' (OSU 1108.001).

The nuts of 'PollyO' are borne in clusters of 3-4 in husks about 25% longer than the nuts (FIG. 4). The husks are slit down the side, and flare open as they dry at maturity (FIG. 6). About 92% of the nuts fall free of the husk at maturity (range 85-97%). The other 8% of the nuts would come out of the husks as they moved through the harvester. When mature, the shells are light tan in color. Nuts in the first trial were hand-harvested and notes recorded at the time of harvest. Notes included the date, the percentage of nuts on the ground (as opposed to in the tree), and the percentage of the nuts on the ground that were free of the husk (as opposed to inside the husk). More than 2000 trees are harvested by hand every fall, visiting a block once every 7 to 10 days, and harvesting a tree if >70% of the nuts are on the ground. Thus the percentages in the first trial are estimates. The harvest dates and percentage down indicate that maturity of 'PollyO' is 10-14 days earlier than 'Barcelona', allowing harvest before the start of the rainy season. To more precisely estimate nut maturity, four trees each of 'PollyO', 'Jefferson' and 'Yamhill' in the first trial and four trees of 'Barcelona' in adjacent rows were harvested by hand at weekly intervals in the final year of the trial (2016). The maturity curves from the 2016 harvest (FIG. 7) show that nuts of 'PollyO' drop a few days earlier than 'Yamhill' and 10-14 days sooner than 'Barcelona'. Average harvest dates compared to 'Barcelona' are about 14 days early for 'McDonald', 10 days early for 'Yamhill' and 7 days early for 'Wepster'. 'Jefferson' nuts mature with 'Barcelona' or up to three days later. Nuts in the second trial were annually raked and fed through a Mave harvester. Prior to harvest, the percentage of nuts on the ground was estimated weekly in the final year of the trial, beginning on September 15 (FIG. 8). The nut drop estimate curves indicate that nut maturity of 'PollyO' is between 'McDonald' and 'Yamhill'. Plantings of 'PollyO' with 'McDonald' and 'Wepster' with additional 'York' pollinizer trees would allow harvest to begin two weeks earlier than 'Barcelona'. Nuts were harvested from four cultivars in the second trial on five dates (FIG. 9), and confirmed the relative maturities. Early harvest before the rainy season begins results in lower drying costs and higher nut quality.

Incompatibility and Pollinizers.

Trees of 'PollyO' set a moderate to high amount of catkins that shed copious amounts of pollen in early mid-season, with 'McDonald', 'Wepster', 'York' and 'Yamhill'. Pollen has been collected and used in several controlled pollinations, and both quantity and viability appear to be very good. Pollen of 'PollyO' has germinated well on agar plates (85% in 2014, 81% in 2015 and 48% in 2017), in contrast to 'Barcelona (36%, 36% and 40%, respectively). 'PollyO' has incompatibility alleles $S_2$ and $S_{10}$ as determined by fluorescence microscopy. Both alleles are expressed in the females, but only $S_{10}$ is expressed in the pollen because of dominance. By convention, alleles expressed in the pollen are underlined.

Time of pollen shed and female receptivity were recorded weekly from mid-December to mid-March and are shown for four years (2014-2018) (FIGS. 10-13). Female inflorescences of 'PollyO' emerged in early mid-season and were fully receptive in mid-January, overlapping the period of receptivity of 'McDonald', 'Wepster', 'Yamhill' and 'York'. Time of pollen shed peaks in the first half of February, about ten days later than the other four cultivars. There would be good overlap between female receptivity and pollen shed for any combination of these five cultivars, which are also cross-compatible in all combinations and directions. Many orchard designs are possible using 'PollyO' ($S_2$ $S_{10}$), 'McDonald' ($S_2$ $S_{15}$) and 'Wepster' ($S_1$ $S_2$). Inclusion of a few trees of the pollinizer 'York' ($S_2$ $S_{21}$) is also recommended. 'Yamhill' ($S_8$ $S_{26}$) is also a suitable pollinizer for 'PollyO' but its tree is lower in vigor and its kernels do not blanch well. Pollen of 'Jefferson' ($S_1$ $S_3$) is also compatible on females of 'PollyO', but 'Jefferson' females emerge very late in the season, and 'Jefferson' has large nuts for the in-shell market whereas all of the others are for the kernel market. Pollen of 'Dorris' ($S_1$ $S_{12}$), 'Sacajawea' ($S_1$ $S_{22}$) and 'Barcelona' ($S_1$ $S_2$) is also compatible on females of 'PollyO'; of these only 'Dorris' is highly resistant to EFB. Pollen of 'Felix' ($S_{15}$ $S_{21}$) and 'Theta' ($S_5$ $S_{15}$) is also compatible but they shed pollen too late to be effective pollinizers for 'PollyO'. Pollen of 'Tonda di Giffoni' ($S_2$ $S_{23}$) (unpatented) is incompatible because it expresses $S_2$. Inclusion of 'McDonald' and 'Wepster' as companion cultivars in the orchard results in no loss in total nut yield. Alternative orchard designs include plantings of different cross-compatible cultivars in adjacent rows. The inclusion of pollinizers with a high level of EFB resistance would eliminate the need for fungicide control in the entire orchard.

Pests and Diseases.

Based on DNA marker data, 'PollyO', like 'McDonald', 'Wepster' and 'Yamhill', has a very high level of resistance to EFB conferred by a dominant allele from 'Gasaway' through the grower selection 'Zimmermean', so fungicide applications are not needed. RAPD markers 152-800 and 268-580 that flank the resistance allele in 'Gasaway' are present in 'PollyO', and these markers are transmitted to its seedlings. Additional RAPD markers linked to resistance are also present. No cankers have been observed on the 11 trees of 'PollyO' in the yield trials, while several cankers have been noted on adjacent trees of susceptible genotypes. During the trials, a nearby heavily infected commercial orchard provided high EFB disease pressure on all plantings. 'PollyO' and many other selections were propagated by tie-off layerage of the suckers in 2013. Eight trees of 'PollyO' were potted and grown in the lathhouse in the summer of 2014 and exposed to EFB under a structure topped with diseased branches in spring 2015. Unfortunately, inspection in December 2016 showed that very few trees became infected, even the highly susceptible check 'Ennis' (unpatented). It seems that the diseased branches were of low-quality inoculum due to freeze injury, as no useful data were provided by this exposure.

Susceptibility to bacterial blight caused by *Xanthomonas campestris* pv. corylina has not been quantified, but no trees in the two trials were affected.

Susceptibility to big bud mite (primarily *Phytoptus avellanae* Nal.) was rated in the first trial (Tables 5-6) after leaf fall once per year for five years (December 2012-2016). The scale was from 1 (no blasted buds) to 5 (many blasted buds), with chemical control considered unnecessary for cultivars with a mean rating <3.3. The average ratings indicate high resistance for 'PollyO' (1.15) and 'Jefferson' (1.34), and an intermediate rating for 'Gamma' (2.96). Blasted buds are very rare on 'PollyO', so chemical applications should not be necessary to control bud mite.

Microsatellite Marker Analysis:

Twenty microsatellite (simple sequence repeat) markers were used. PCR products were multiplexed post-PCR and sized using capillary electrophoresis (Tables 12-13, and see for example Bassil et al., *Acta Horticulturae* 686:105-110, 2005; Gökirmak et al., *Genetic Resources and Crop Evolution* 56:147-172, 2009; Gürcan and Mehlenbacher. *Molecular Breeding* 26:551-559, 2010; Gürcan et al. *Tree Genetics and Genomes* 6:513-531, 2010).

TABLE 12

Primers for the microsatellite marker loci used to fingerprint 'PollyO' and other hazelnut cultivars.

| Set | Locus | Repeat Motif | Allele sizes | Primers (5'-3') (SEQ ID NO:) | |
|---|---|---|---|---|---|
| 3 | A613 | $(TC)_{13}(CA)_{12}$ | 149-177 | Ned-CACACGCCTTGTCACTCTTT(1) | R-CCCCTTTCACATGTTTGCTT(2) |
| 2 | A614 | $(TC)_{17}(CA)_{10}$ NNN$(CA)_6$ | 125-156 | Hex-TGGCAGAGCTTTGTCAGCTT(3) | R-GCAGTGGAGGATTGCTGACT(4) |

TABLE 12-continued

Primers for the microsatellite marker loci used to fingerprint 'PollyO' and other hazelnut cultivars.

| Set | Locus | Repeat Motif | Allele sizes | Primers (5'-3') (SEQ ID NO:) | |
|---|---|---|---|---|---|
| 3 | A616 | $(AC)_{11}$ | 136-162 | Fam-CACTCATACCGCAAACTCCA(5) | R-ATGGCTTTTGCTTCGTTTTG(6) |
| 1 | A640 | $(CT)_{15}(CA)_{13}$ | 354-378 | F-TGCCTCTGCAGTTAGTCATCAAATGTAGG(7) | Fam-CGCCATATAATTGGGATGCTTGTTG(8) |
| 3 | B617 | $(GA)_{15}$ | 280-298 | Fam-TCCGTGTTGAGTATGGACGA(9) | R-TGTTTTTGGTGGAGCGATG(10) |
| 2 | B619 | $(TC)_{21}$ | 146-180 | Fam-AGTCGGCTCCCCTTTTCTC(11) | R-GCGATCTGACCTCATTTTTG(12) |
| 4 | B634 | $(AG)_{15}$ | 218-238 | Hex-CCTGCATCCAGGACTCATTA(13) | R-GTGCAGAGGTTGCACTCAAA(14) |
| 4 | B657 | $(AG)_{15}$ | 210-228 | Ned-GAGAGTGCGTCTTCCTCTGG(15) | R-AGCCTCACCTCCAACGAAC(16) |
| 3 | B671 | $(AG)_6NN(GA)_{17}$ | 221-249 | Hex-TTGCCAGTGCATACTCTGATG(17) | R-ACCAGCTCTGGGCTTAACAC(18) |
| 2 | B709 | $(GA)_{21}$ | 219-233 | Ned-CCAAGCACGAATGAACTCAA(19) | R-GCGGGTTCTCGTTGTACACT(20) |
| 1 | B733 | $(TC)_{15}$ | 161-183 | Ned-CACCCTCTTCACCACCTCAT(21) | R-CATCCCCTGTTGGAGTTTTC(22) |
| 2 | B749 | $(TC)_{12}$ | 200-210 | Hex-GGCTGACAACACAGCAGAAA(23) | R-TCGGCTAGGGTTAGGGTTTT(24) |
| 4 | B751 | $(GA)_{15}$ | 141-153 | Fam-AGCTGGTTCTTCGACATTCC(25) | R-AAACTCAAATAAAACCCCTGCTC(26) |

TABLE 12-continued

Primers for the microsatellite marker loci used to fingerprint 'PollyO' and other hazelnut cultivars.

| Set | Locus | Repeat Motif | Allele sizes | Primers (5'-3') (SEQ ID NO:) | |
|---|---|---|---|---|---|
| 1 | B774 | $(AG)_{15}$ | 195-213 | Ned-GTTTTGCGAGCTCATTGTCA(27) | R-TGTGTGTGGTCTGTAGGCACT(28) |
| 3 | C115 | $(TAA)_5(GAA)_{12}$ | 167-225 | Fam-CATTTTCCGCAGATAATACAGG(29) | R-GTTTCCAGATCTGCCTCCATATAAT(30) |
| 3 | KG807 | $(TAAA)AA(TAAA)_2A(TAAA)_2$ | 226-248 | F-AAGCAAGAAAGGGATGGT(31) | Fam-CTTACAGATAAATGGCTCAAA(32) |
| 1 | KG809 | $(AGG)_6$ | 333-345 | F-GGAAGGTGAGAGAAATCAAGT(33) | Hex-AGGCATCAGTTCATCCAA(34) |
| 2 | KG811 | $(GA)_{17}$ | 240-278 | F-GAACAACTGAAGACAGCAAAG(35) | Ned-AAGGCGGCACTCGCTCAC(36) |
| 4 | KG827 | $(CT)_{13}AA(CA)_7$ | 264-282 | Fam-AGAACTCCGACTAATAATCCTAACCCTTGC(37) | R-GAGGGAGCAAGTCAAAGTTGAGAAGAAA(38) |
| 2 | KG830 | $(CT)_{14}GTATT(CA)_8$ | 279-311 | Ned-TGGAGGAAGTTTTGAATGGTAGTAGAGGA(39) | R-AAAGCAACTCATAGCTGAAGTCCAATC(40)A |

Set = Multiplex set, with samples mixed after PCR but before submission for sizing by capillary electrophoresis; Allele size = range of sizes; Primers, forward (F, listed first) and reverse (R, second) (Hex and Fam are dyes).

TABLE 13

Annealing temperatures for the microsatellite marker loci used to fingerprint 'PollyO' and other hazelnut cultivars.

| Set | Tm (° C.) | n | He | Ho | PIC | r | LG | Locus | Reference |
|---|---|---|---|---|---|---|---|---|---|
| 3 | 60 | 14 | 0.86 | 0.85 | 0.85 | 0.00 | 11R | A613 | Gurcan et al., 2010 |
| 2 | 60 | 14 | 0.85 | 0.85 | 0.84 | 0.00 | 65,6R | A614 | Gurcan et al., 2010 |
| 3 | 60 | 13 | 0.85 | 0.85 | 0.83 | 0.00 | 8R | A616 | Gurcan et al., 2010 |
| 1 | 67 | 11 | 0.80 | 0.73 | 0.77 | 0.04 | lOR | A640 | Gurcan et al., 2010 |
| 3 | 60 | 9 | 0.80 | 0.78 | 0.78 | 0.01 | 85,8R | B617 | Gurcan et al., 2010 |
| 2 | 60 | 14 | 0.88 | 0.88 | 0.87 | 0.00 | 35,3R | B619 | Gurcan et al., 2010 |

TABLE 13-continued

Annealing temperatures for the microsatellite marker loci used to fingerprint 'PollyO' and other hazelnut cultivars.

| Set | Tm (° C.) | n | He | Ho | PIC | r | LG | Locus | Reference |
|---|---|---|---|---|---|---|---|---|---|
| 4 | 60 | 9 | 0.76 | 0.76 | 0.73 | 0.00 | 4R | B634 | Gurcan et al., 2010 |
| 4 | 60 | 8 | 0.84 | 0.98 | 0.82 | −0.08 | 11S,11 | B657 | Gurcan et al., 2010 |
| 3 | 60 | 13 | 0.86 | 0.88 | 0.84 | −0.01 | 95,9R | B671 | Gurcan et al., 2010 |
| 2 | 60 | 8 | 0.74 | 0.76 | 0.70 | −0.01 | 55,5R | B709 | Gurcan et al., 2010 |
| 1 | 60 | 8 | 0.68 | 0.68 | 0.63 | 0.00 | 75,2R | B733 | Gurcan et al., 2010 |
| 2 | 60 | 6 | 0.60 | 0.64 | 0.51 | −0.03 | 1R | B749 | Gurcan et al., 2010 |
| 4 | 60 | 7 | 0.80 | 0.78 | 0.77 | 0.01 | 75,2R | B751 | Gurcan et al., 2010 |
| 1 | 60 | 8 | 0.80 | 0.80 | 0.77 | 0.00 | 55,5R | B774 | Gurcan et al., 2010 |
| 3 | 60 | 10 | 0.84 | 0.90 | 0.82 | 0.035 | 45,4R | C115 | B assil et al., 2005b; Gokirmak et al., 2009 |
| 3 | 54 | 4 | 0.67 | 0.78 | 0.60 | −0.07 | 11 | KG807 | Gurcan and Mehlenbacher, 2010 |
| 1 | 55 | 5 | 0.66 | 0.64 | 0.60 | 0.01 | 4 | KG809 | Gurcan and Mehlenbacher, 2010 |
| 2 | 58 | 12 | 0.83 | 0.82 | 0.81 | 0.01 | 2 | KG811 | Gurcan and Mehlenbacher, 2010 |
| 4 | 67 | 9 | 0.78 | 0.84 | 0.75 | −0.04 | 9 | KG827 | Gurcan and Mehlenbacher, 2010 |
| 2 | 67 | 9 | 0.79 | 0.78 | 0.76 | 0.00 | 9 | KG830 | Gurcan and Mehlenbacher, 2010 |

Tm = Annealing temperature ; n = Number of alleles; He = expected heterozygosity; Ho = observed heterozygosity; PIC = Polymorphism information content; r = frequency of null alleles; LG = linkage group (S is susceptible female parent 'OSU 252.146'; R is resistant parent 'OSU 414.062'); Reference is the journal article where additional details were published.

Table 14 shows allele sizes at 20 microsatellite markers for 'PollyO', its parents 'OSU684.104' and 'OSU 669.104', cultivars and selections that appear in the pedigree of 'PollyO' ('Mortarella' to 'Montebello'), and four kernel cultivars ('Yamhill', 'Tonda Pacifica', 'McDonald' and 'Wepster'). 'PollyO' is easily distinguished from all others shown in Table 13. 'PollyO' is different from its female parent 'OSU 684.104' at 11 of the 20 marker loci. 'PollyO' is different from its male parent 'OSU 669.104' at 14 of the 20 marker loci. 'PollyO' is the same as both parents at 3 loci. 'PollyO' is the same as one parent at 9 loci. 'PollyO' is different from both parents at 8 loci. Allele A614-125, Allele A616-144, Allele B617-285, Alleles B709-223 and B709-227, and Allele KG807-238 observed in 'PollyO' are not found any of 'Yamhill', 'Tonda Pacifica', 'McDonald', and 'Wepster'.

TABLE 14

Allele sizes at 20 microsatellite markers

| Marker | 'PollyO' | 'OSU 684.104' | 'OSU 669.104' | 'Mortarella' |
|---|---|---|---|---|
| A613 | 153/167 | 153/167 | 153/153 | 151/153 |
| A614 | 125/158 | 125/132 | 132/158 | 132/135 |
| A616 | 144/152 | 150/152 | 144/150 | 150/158 |
| A640 | 354/354 | 354/374 | 354/354 | 354/374 |
| B617 | 285/295 | 285/293 | 289/295 | 293/295 |
| B619 | 158/166 | 158/178 | 166/176 | 158/172 |
| B634 | 228/236 | 236/236 | 222/228 | 228/236 |
| B657 | 218/218 | 218/218 | 218/218 | 218/224 |
| B671 | 229/249 | 225/249 | 229/237 | 225/243 |
| B709 | 223/227 | 223/229 | 227/229 | 221/229 |
| B733 | 175/181 | 175/175 | 175/181 | 175/175 |
| B749 | 216/216 | 216/216 | 214/216 | 214/216 |
| B751 | 144/154 | 144/154 | 154/154 | 144/154 |
| B774 | 209/209 | 209/215 | 209/215 | 209/220 |
| C115 | 194/215 | 194/215 | 174/215 | 182/215 |
| KG807 | 238/252 | 238/252 | 238/252 | 230/234 |
| KG809 | 342/342 | 342/342 | 339/342 | 342/342 |
| KG811 | 261/267 | 261/267 | 261/267 | 261/267 |
| KG827 | 272/284 | 272/282 | 272/284 | 282/282 |
| KG830 | 291/295 | 291/295 | 295/295 | 291/307 |

| Marker | 'OSU 14.084' | 'Negret' | 'Barcelona' | 'Daviana' | 'OSU 342.019' |
|---|---|---|---|---|---|
| A613 | 153/167 | 153/159 | 153/161 | 167/179 | 153/153 |
| A614 | 125/148 | 132/132 | 125/132 | 148/150 | 125/132 |
| A616 | 144/152 | 152/160 | 144/152 | 150/152 | 144/160 |
| A640 | 354/354 | 354/368 | 354/374 | 354/354 | 354/354 |
| B617 | 289/295 | 285/291 | 285/289 | 289/295 | 293/295 |
| B619 | 172/178 | 166/170 | 158/172 | 168/178 | 158/166 |
| B634 | 228/236 | 228/234 | 228/228 | 228/236 | 228/232 |
| B657 | 218/226 | 218/222 | 218/222 | 218/226 | 218/218 |
| B671 | 229/249 | 229/237 | 225/229 | 239/249 | 229/229 |
| B709 | 229/235 | 223/227 | 227/235 | 229/229 | 227/227 |
| B733 | 173/181 | 167/175 | 173/175 | 173/181 | 175/181 |
| B749 | 216/216 | 216/216 | 216/216 | 216/216 | 214/216 |
| B751 | 144/152 | 152/154 | 144/154 | 144/152 | 152/154 |
| B774 | 213/213 | 209/215 | 209/213 | 213/215 | 209/213 |
| C115 | 174/194 | 182/215 | 174/194 | 174/194 | 174/197 |
| KG807 | 252/252 | 238/252 | 238/252 | 238/252 | 238/252 |
| KG809 | 339/342 | 339/342 | 339/339 | 339/342 | 339/342 |
| KG811 | 261/267 | 259/267 | 261/267 | 255/261 | 267/267 |
| KG827 | 272/284 | 272/284 | 282/284 | 272/272 | 284/284 |
| KG830 | 295/295 | 295/303 | 291/295 | 289/295 | 295/295 |

| Marker | 'Zimmerman' | 'Gasaway' | 'Casina' | 'Montebello' |
|---|---|---|---|---|
| A613 | 153/163 | 161/163 | 151/153 | 151/153 |
| A614 | 132/158 | 143/158 | 125/139 | 125/132 |
| A616 | 144/150 | 150/150 | 144/152 | 152/160 |
| A640 | 354/368 | 362/368 | 354/372 | 362/374 |
| B617 | 289/295 | 291/295 | 285/295 | 285/293 |
| B619 | 172/176 | 172/176 | 150/158 | 160/166 |
| B634 | 222/228 | 222/234 | 228/232 | 232/236 |
| B657 | 218/224 | 224/228 | 216/218 | 218/226 |
| B671 | 229/237 | 237/249 | 229/249 | 225/243 |
| B709 | 229/235 | 229/229 | 227/233 | 229/235 |
| B733 | 175/175 | 175/175 | 175/175 | 175/185 |
| B749 | 216/216 | 214/216 | 214/216 | 216/216 |
| B751 | 144/154 | 144/144 | 152/154 | 154/154 |
| B774 | 213/215 | 209/215 | 209/215 | 209/213 |
| C115 | 174/215 | 215/218 | 174/197 | 174/197 |
| KG807 | 238/252 | 242/252 | 238/252 | 238/242 |
| KG809 | 339/339 | 339/348 | 339/339 | 339/348 |
| KG811 | 261/267 | 257/261 | 251/267 | 251/267 |
| KG827 | 272/284 | 272/282 | 272/284 | 282/282 |
| KG830 | 295/305 | 291/305 | 295/303 | 291/295 |

| Marker | 'Yamhill' | 'Tonda Pacifica' | 'McDonald' | 'Wepster' |
|---|---|---|---|---|
| A613 | 153/163 | 159/169 | 153/169 | 159/167 |
| A614 | 132/158 | 135/150 | 135/158 | 135/158 |
| A616 | 150/150 | 150/160 | 150/160 | 152/160 |
| A640 | 354/368 | 368/374 | 362/368 | 368/374 |

TABLE 14-continued

| Allele sizes at 20 microsatellite markers | | | | |
|---|---|---|---|---|
| B617 | 289/295 | 293/295 | 293/295 | 293/295 |
| B619 | 158/172 | 166/172 | 158/172 | 166/172 |
| B634 | 236/236 | 228/228 | 222/228 | 228/228 |
| B657 | 218/228 | 210/226 | 210/218 | 226/226 |
| B671 | 225/243 | 229/239 | 229/237 | 239/249 |
| B709 | 229/229 | 229/235 | 229/229 | 229/235 |
| B733 | 181/185 | 173/175 | 173/175 | 173/175 |
| B749 | 216/216 | 214/216 | 214/216 | 214/216 |
| B751 | 152/152 | 144/154 | 144/144 | 144/144 |

TABLE 14-continued

| Allele sizes at 20 microsatellite markers | | | | |
|---|---|---|---|---|
| B774 | 209/217 | 209/213 | 209/220 | 209/213 |
| C115 | 197/215 | 174/182 | 174/197 | 182/194 |
| KG807 | 230/252 | 228/252 | 252/252 | 252/252 |
| KG809 | 348/348 | 339/342 | 339/339 | 342/342 |
| KG811 | 251/261 | 245/257 | 245/267 | 257/257 |
| KG827 | 282/282 | 270/284 | 272/284 | 270/282 |
| KG830 | 291/295 | 291/295 | 291/295 | 295/305 |

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

cacacgcctt gtcactcttt                                                20


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

ccccttttcac atgtttgctt                                               20


<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3

tggcagagct ttgtcagctt                                                20


<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4

gcagtggagg attgctgact                                                20


<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

cactcatacc gcaaactcca                                                20
```

-continued

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6 atggcttttg cttcgttttg 20

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7 tgcctctgca gttagtcatc aaatgtagg 29

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8 cgccatataa ttgggatgct tgttg 25

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9 tccgtgttga gtatggacga 20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10 tgtttttggt ggagcgatg 19

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11 agtcggctcc ccttttctc 19

<210> SEQ ID NO 12
<211> LENGTH: 20
<212> TYPE: DNA
<213> ORGANISM: Artificial Sequence
<220> FEATURE:

-continued

<223> OTHER INFORMATION: Primer

<400> SEQUENCE: 12 gcgatctgac ctcatttttg 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13 cctgcatcca ggactcatta 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14 gtgcagaggt tgcactcaaa 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15 gagagtgcgt cttcctctgg 20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16 agcctcacct ccaacgaac 19

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17 ttgccagtgc atactctgat g 21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18 accagctctg ggcttaacac 20

-continued

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19 ccaagcacga atgaactcaa 20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 gcgggttctc gttgtacact 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 caccctcttc accacctcat 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 catcccctgt tggagttttc 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23 ggctgacaac acagcagaaa 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24 tcggctaggg ttagggtttt 20

<210> SEQ ID NO 25
<211> LENGTH: 23
<212> TYPE: DNA
<213> ORGANISM: Artificial Sequence
<220> FEATURE:

-continued

<223> OTHER INFORMATION: Primer

<400> SEQUENCE: 25 aaactcaaat aaaacccctg ctc 23

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26 aaactcaaat aaaacccctg ctc 23

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27 gttttgcgag ctcattgtca 20

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28 tgtgtgtggt ctgtaggcac t 21

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29 cattttccgc agataataca gg 22

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30 gtttccagat ctgcctccat ataat 25

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31 aagcaagaaa gggatggt 18

-continued

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32 cttacagata aatggctcaa a 21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33 ggaaggtgag agaaatcaag t 21

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34 aggcatcagt tcatccaa 18

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35 gaacaactga agacagcaaa g 21

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36 aaggcggcac tcgctcac 18

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37 agaactccga ctaataatcc taacccttgc 30

<210> SEQ ID NO 38
<211> LENGTH: 28
<212> TYPE: DNA
<213> ORGANISM: Artificial Sequence
<220> FEATURE:

-continued

```
<223> OTHER INFORMATION: Primer

<400> SEQUENCE: 38

gagggagcaa gtcaaagttg agaagaaa                                    28


<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39

tggaggaagt tttgaatggt agtagagga                                   29


<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40

aaagcaactc atagctgaag tccaatc                                     27
```

We claim:

1. A new and distinct cultivar of *Corylus* plant as illustrated and described.

* * * * *

FIG. 10

Phenology Chart 1. Time of female receptivity (bottom red) and pollen shed (top green) from Dec 2014-Mar 2015 of selections in the second trial planted in 2011, including its guard row.

| | Dec | | | Jan | | | | | | Feb | | | | | March | | | | |
|---|---|---|---|---|---|---|---|---|---|---|---|---|---|---|---|---|---|---|---|
| Genotype | 15-Dec | 22-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 3-Mar | 7-Mar | 11-Mar | 18-Mar | 27-Mar |
| 11108.001 | | | | | | | | 1st | 5 | 20 | 70 | 100-10 | 100-90 | gr tip | BB | | | | |
| (2, 10) | | Rd | | | Rd+2 | | I+2 | I+2/S+2 | | I+3/S+2 | I/S+3 | | | | | | | | |
| | | | | | | | Red | | | Red | Black | | | | | | | | |
| Wepster | | | | | 1st | | 5 | 70 | 100-20 | | gr tip | | | | BB | | | | |
| 1, 2 | Rd | Rd+3 | Rd+2/I | | Rd+3/I | | | Rd/I+3/S | I+3/S | | | S+3 | | | | | | | |
| | | | Red | | | | Red | | dk | | | dk/black | | Black | | | | | |
| McDonald | | | | 1st | 10 | 30 | 70 | 100-20 | 100-80 | | gr tip | | | | BB | | | | |
| 2, 15 | Rd+2 | | | Rd+2 | Rd+3/I | | Rd/I+2 | I+3/S | I+2/S+2 | I/S+3 | | | | S+3 | | | | | |
| | | | | | | | Red | | | Red/dark | dark | | | dk/black | | | | | |
| York | | | | | | | 1st | 40 | 75 | 95-20 | -80 | | gr tip | | BB | | | | |
| 2, 21 | | Rd | | | Rd+2/I | | Rd+2/I | Rd/I+2 | I+3 | I+3/S | I+3/S | | | | | | | | |
| | | | | | | | dark | | | | Black | | | | | | | | |
| Yarnhill | | | 5 | | 40 | 60 | 70 | 95-20 | 100-40 | 100-70 | gr tip | | BB | | | | | | |
| 8, 26 | Rd-few | | Rd+/I+ | | I+3 | I+3/S+ | I+3/S+2 | | | I+3/S+2 | | I/S+3 | | | | | | | |
| | | | Red | | | | | Red | | dk | | Black | | | | | | | |
| Jefferson | | | | | | | | 10 | 50 | 100 | -70 | | | | | | | | |
| 1, 3 | | | | | | | Rd | | Rd+3 | Rd+3/I | I+2/S | I+2/S+2 | | S+3 | | | | | |
| | | | | | | | | | | Red | | Red/dk | | | Black | | | | |

Flower stages: RD = Red dot; I = styles protruding ~1-3mm, straight; FS = First appearance of 'spiders' or flowers with reflexed styles, and S+3 = majority of flowers are in 'spider' or fully reflexed stage.

Green = Pollen shed (a minus sign in front of the number indicates the percent of catkins that have already shed out).

Red = Female flowers; red, blk (black), dk (dark, not quite red, not yet black).

BB = leaf budbreak

FIG. 12

Phenology Chart 3. Time of female receptivity (bottom red) and pollen shed (top green) from Dec 2016-Mar 2017 of selections in the second trial planted in 2011, including its guard row.

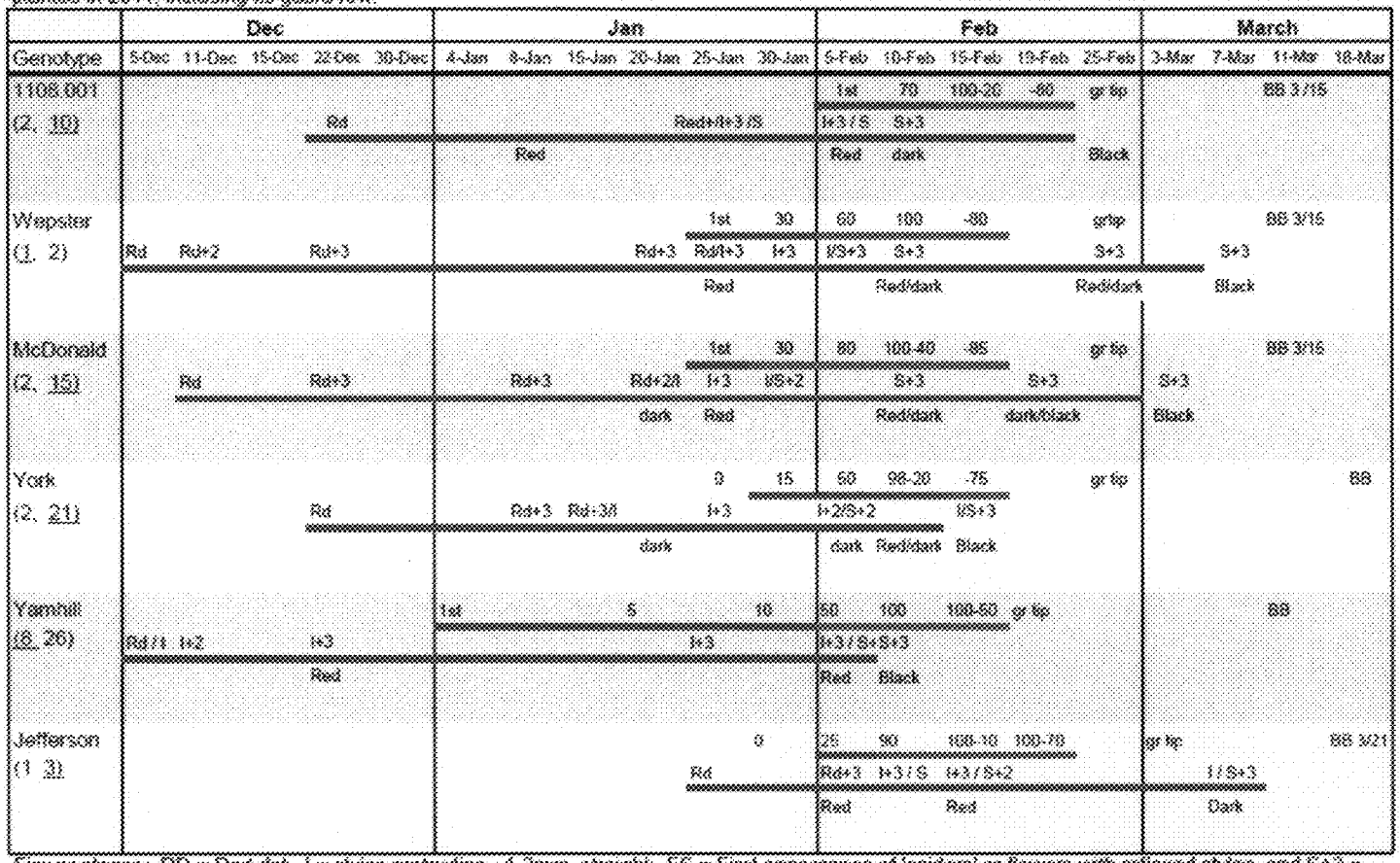

Flower stages: RD = Red dot, I = styles protruding ~ 1-3mm, straight, FS = First appearance of 'spiders' or flowers with reflexed styles, and S+3 = majority of flowers are in 'spider' or fully reflexed stage.

Green = Pollen shed (a minus sign in front of the number indicates the percent of catkins that have already shed out).

Red = Female flowers: red, blk (black), dk (dark, not quite red, not yet black).

BB = Leaf budbreak